United States Patent
Tsutsumi et al.

(10) Patent No.: US 11,220,679 B2
(45) Date of Patent: Jan. 11, 2022

(54) POLYPEPTIDES HAVING TREHALASE ACTIVITY

(71) Applicant: NOVOZYMES A/S, Bagsvaerd (DK)

(72) Inventors: Noriko Tsutsumi, Chiba (JP); Tomoko Matsui, Chiba (JP); Yuma Kurakata, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/635,195

(22) PCT Filed: Aug. 6, 2018

(86) PCT No.: PCT/EP2018/071257
§ 371 (c)(1),
(2) Date: Jan. 30, 2020

(87) PCT Pub. No.: WO2019/030165
PCT Pub. Date: Feb. 14, 2019

(65) Prior Publication Data
US 2021/0087543 A1    Mar. 25, 2021

(30) Foreign Application Priority Data
Aug. 8, 2017 (EP) ..................... 17185362

(51) Int. Cl.
*C12N 9/24* (2006.01)
*C12P 19/14* (2006.01)

(52) U.S. Cl.
CPC ............ *C12N 9/2402* (2013.01); *C12P 19/14* (2013.01); *C12Y 302/01028* (2013.01)

(58) Field of Classification Search
None
See application file for complete search history.

(56) References Cited

U.S. PATENT DOCUMENTS 10,676,727 B2 * 6/2020 Kang .................. C12N 9/2402

FOREIGN PATENT DOCUMENTS

| WO | 2009/121058 A1 | 10/2010 |
|---|---|---|
| WO | 2012/027374 A2 | 3/2012 |
| WO | 2012/080100 A1 | 6/2012 |
| WO | 2013/036526 A2 | 3/2013 |
| WO | 2013/148993 A1 | 10/2013 |
| WO | 2015/065978 A1 | 5/2015 |
| WO | 2016/205127 A1 | 12/2016 |
| WO | 2017/116840 A1 | 7/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter26:Unit26.7. (Year: 2011).*
Yoshikuni et al. Curr Opin Chem Biol. Apr. 2007;11(2):233-9. (Year: 2007).*
Aeschbacher et al, 1999, Plant Physiol 119, 489-496.
Amaral et al, 1996, Can J Microbiol 41, 1057-1062.
Berka et al, 2011, EBI accession No. G2RDT9.
Cardello et al, 1994, Microbiology 140, 1671-1677.
Cheng et al, 2016, BMC Biotechnology 16(1), 1-8.
D'Enfert et al, 1997, Mol Microbiol 24, 203-216.
Dewerchin et al, 1984, J Bacteriol 158, 575-579.
Grba et al, 1975, Eur J Appl Microbiol 2, 29-37.
Hecker et al, 1973, J Bacteriol 115, 592-599.
Kadowaki et al, 1996, Biochim Biophys Acta 1291, 199-205.
Londesborough et al, 1984, Biochem J 219, 511-518.
Parvaeh et al, 1996, FEBS Lett 391, 273-278.
Sumida et al, 1989, J Ferm Bioeng 67, 83-86.
Thevelein et al, 1983, J Gen Microbiol 129, 719-726.
Uhland et al, 2000, J Biol Chem 275(31), 23439-23445.
Zimmermann et al, 1990, Biochim Biophys Acta 1036, 41-46.

* cited by examiner

*Primary Examiner* — Christian L Fronda
(74) *Attorney, Agent, or Firm* — David A. Fazzolare

(57) ABSTRACT

The present invention relates to trehalase variants of the *Myceliophthora sepedonium* GH37 trehalase. The present invention also relates to polynucleotides encoding the variants; nucleic acid constructs, vectors, and host cells comprising the polynucleotides; and methods of using the variants.

17 Claims, No Drawings
Specification includes a Sequence Listing.

POLYPEPTIDES HAVING TREHALASE ACTIVITY

CROSS-REFERENCE TO RELATED APPLICATIONS

This application is a 35 U.S.C. 371 national application of international application no. PCT/EP2018/071257 filed Aug. 6, 2018, which claims priority or the benefit under 35 U.S.C. 119 of European application no. 17185362.5 filed Aug. 8, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having trehalase activity and polynucleotides encoding the polypeptides. The invention also relates to nucleic acid constructs, vectors, and host cells comprising the polynucleotides as well as methods of producing the polypeptides. The invention also relates to processes of producing fermentation products using a trehalase of the invention.

Description of Background Art

The present invention provides trehalase enzyme variants with improved properties compared to its parent. Trehalose is a stable disaccharide sugar consisting of two sugar monomers (glucose). Trehalose is accumulated in yeast as a response to stress in up to 10-15% of cell dry weight (GrBa et al. (1975) Eur. J. Appl. Microbiol. 2:29-37). Trehalose cannot be metabolized by the yeast. The enzyme trehalase cleaves trehalose into two glucose units.

Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on "http://www.expasy.org/enzyme/". The two enzyme classes are both referred to as "trehalases". Examples of neutral trehalases include trehalases from *Saccharomyces cerevisiae* (Londesborouh et al. (1984) Characterization of two trehalases from baker's yeast" Biochem J 219, 511-518; *Mucor roxii* (Dewerchin et al (1984), "Trehalase activity and cyclic AMP content during early development of *Mucor rouxii* spores", J. Bacteriol. 158, 575-579); *Phycomyces blakesleeanus* (Thevelein et al (1983), "Glucose-induced trehalase activation and trehalose mobilization during early germination of *Phycomyces blakesleeanus* spores" J. Gen Microbiol. 129, 719-726); *Fusarium oxysporium* (Amaral et al (1996), "Comparative study of two trehalase activities from *Fusarium oxysporium* var *linii*" Can. J Microbiol. 41, 1057-1062). Examples of neutral trehalases include, but are not limited to, trehalases from *Saccharomyces cerevisiae* (Parvaeh et al. (1996) Purification and biochemical characterization of the ATH1 gene product, vacuolar acid trehalase from *Saccharomyces cerevisae*" FEBS Lett. 391, 273-278); *Neorospora crassa* (Hecker et al (1973), "Location of trehalase in the ascospores of *Neurospora*: Relation to ascospore dormancy and germination". J. Bacteriol. 115, 592-599); *Chaetomium aureum* (Sumida et al. (1989), "Purification and some properties of trehalase from *Chaetomium aureum* MS-27. J. Ferment. Bioeng. 67, 83-86); *Aspergillus nidulans* (d'Enfert et al. (1997), "Molecular characterization of the *Aspergillus nidulans* treA gene encoding an acid trehalase required for growth on trehalose. Mol. Microbiol. 24, 203-216); *Humicola grisea* (Zimmermann et al. (1990). "Purification and properties of an extracellular conidial trehalase from *Humicola grisea* var. *thermoidea*", Biochim. Acta 1036, 41-46); *Humicola grisea* (Cardello et al. (1994), "A cytosolic trehalase from the thermophilhilic fungus *Humicola grisea* var. *thermoidea*', Microbiology UK 140, 1671-1677; *Scytalidium thermophilum* (Kadowaki et al. (1996), "Characterization of the trehalose system from the thermophilic fungus *Scytalidium thermophilum*" Biochim. Biophys. Acta 1291, 199-205); and *Fusarium oxysporium* (Amaral et al (1996), "Comparative study of two trehalase activities from *Fusarium oxysporium* var *linii*" Can. J Microbiol. 41, 1057-1062).

A trehalase is also know from soybean (Aeschbachet et al (1999) "Purification of the trehalase GmTRE1 from soybean nodules and cloning of its cDNA", Plant Physiol 119, 489-496).

Trehalases are also present in small intestine and kidney of mammals.

WO 2009/121058 (Novozymes) concerns a method of fermenting sugars derived from plant material into a fermentation product, such as ethanol, using a fermenting organism by adding one or more trehalase into in the fermentation medium.

WO 2012/027374 (Dyadic) discloses a trehalase from *Myceliophthora thermophila* which can be used in an enzyme mixture for degrading lignocellulosic biomass to fermentable sugars.

WO 2013/148993 (Novozymes) discloses a process of producing a fermentation product, such as ethanol, from starch-containing material by liquefying, saccharifying and fermenting the starch-containing material wherein a carbohydrate-source generating enzyme, a cellulolytic composition and a trehalase is present in fermentation. A trehalase from *Trichoderma reesei* is disclosed.

WO 2015/065978 (Danisco US Inc.) discloses a method of increasing the production of ethanol from a liquefact in a fermentation reaction including fermenting the liquefact with a glucoamylase, a fermenting organism and a trehalase and recovering the ethanol and other fermentation products at the end of the fermentation.

WO 2016/205127 (Novozymes) discloses a trehalase from *Myceliophthora sepedonium* belonging to Family 37 Glucoside Hydrolases ("GH37") as defined by CAZY (see www.cazy.org), having high thermostability and a broad pH range. It was also found that an increased ethanol yield can be obtained when adding a trehalase to fermentation in an ethanol process.

There is still a need for providing improved trehalase enzymes or enzyme composition suitable for use in processes for producing fermentation products, such as ethanol, in increased yields.

SUMMARY OF THE INVENTION

The present invention relates to a trehalase variant polypeptide having increased stability against protease degradation and/or increased thermo-stability, comprising a substitution at one or more positions corresponding to position 152, 182, 185, or 583 of SEQ ID NO: 1, wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity.

The present invention also relates to polynucleotides encoding the variants; nucleic acid constructs, vectors, and host cells comprising the polynucleotides; and methods of producing the variants. The present invention also relates to compositions comprising the variant polypeptide of the invention.

The present invention also relates to a process of producing a fermentation product, comprising
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of the invention;
iii) optionally a cellulolytic enzyme composition and/or a protease;
are present and/or added during
  saccharification step (b);
  fermentation step (c);
  simultaneous saccharification and fermentation;
  optionally presaccharification step before step (b).

The present invention also relates to a process of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase, alpha-amylase, variant trehalase of the invention, and optionally a protease and/or a cellulolytic enzyme composition.

The present invention also relates to a process of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product, wherein a variant trehalase of the invention is added and/or present in hydrolysis step (a) and/or fermentation step (b).

Definitions

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on "http://www.expasy.org/enzyme/". Trehalases are enzymes that catalyze the following reactions:
EC 3.2.1.28:
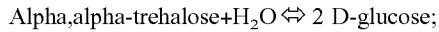
EC 3.2.1.93:
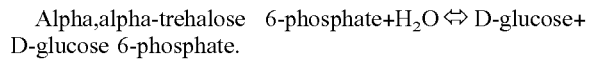

For purposes of the present invention, trehalase activity may be determined according to "Trehalase Assay" procedure described in the "Materials & Methods"-section. In one aspect, the polypeptides of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 1. In a preferred embodiment a trehalase of the invention is a Family 37 Glycoside Hydrolase ("GH37 trehalase").

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme. In one embodiment the catalytic domain is amino acids 105 to 608 of SEQ ID NO: 1.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA. In one embodiment the cDNA is SEQ ID NO: 3 herein.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has trehalase activity. In one aspect, a fragment contains at least 504 amino acid residues (e.g., amino acids 105 to 608 of SEQ ID NO: 1).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. In particular the host cell is a recombinant host cell. Particularly the recombinant host cell comprises the polynucleotide encoding a variant of the present invention in which the said polynucleotide is heterologous (of different origin/species) to the host cell. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to increased thermostability and increased stability against protease degradation, in particular degradation by *Aspergillus niger* protease mixture.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 674 of SEQ ID NO: 1. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having trehalase activity. In one aspect, the mature polypeptide coding sequence is nucleotides 61 to 2022 of SEQ ID NO: 2.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent trehalase: The term "parent" or "parent trehalase" means any polypeptide with trehalase activity to which an alteration is made to produce the enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment–Total Number of Gaps in Alignment)

Stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having trehalase activity.

Variant: The term "variant" means a polypeptide having trehalase activity comprising an alteration, i.e., a substitution, insertion, and/or deletion, at one or more (e.g., several)

positions. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 1.

Wild-type trehalase: The term "wild-type" trehalase means a trehalase expressed by a naturally occurring microorganism, such as a bacterium, yeast, or filamentous fungus found in nature.

Conventions for Designation of Variants

For purposes of the present invention, the mature polypeptide disclosed as SEQ ID NO: 1 is used to determine the corresponding amino acid residue in another trehalase. The amino acid sequence of another trehalase is aligned with the polypeptide disclosed in SEQ ID NO: 1, and based on the alignment, the amino acid position number corresponding to any amino acid residue in the mature polypeptide disclosed as SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in trehalase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to trehalase variants, comprising a substitution at one or more (e.g., several) positions corresponding to positions 152, 182, 185 and 583 of the polypeptide of SEQ ID NO: 1, wherein the variant has trehalase activity. In particular the variant trehalase of the invention has increased stability against protease degradation and/or increased thermo-stability compared to the trehalase of SEQ ID NO: 1.

Variants

The present invention provides trehalase variants, comprising a substitution at one or more (e.g., several) positions corresponding to positions 152, 182, 185, and 583, wherein the variant has trehalase activity.

In an embodiment, the variant has sequence identity of at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent trehalase.

In another embodiment, the variant has at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1.

In one aspect, the number of alterations in the variants of the present invention is 1-20, e.g., 1-10 and 1-5, such as 1, 2, 3, 4, 5, 6, 7, 8, 9 or 10 substitutions.

In another aspect, a variant comprises a substitution at one or more (e.g., several) positions corresponding to positions 152, 182, 185, and 583. In another aspect, a variant comprises substitution at two positions corresponding to any of positions 152, 182, 185, and 583. In another aspect, a variant comprises a substitution at three positions corresponding to any of positions 152, 182, 185, and 583. In another aspect, a variant comprises a substitution at each position corresponding to positions 152, 182, 185, and 583.

In another aspect, the variant comprises or consists of a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Ser, Thr, Trp, Tyr, or Val, preferably with Ala, Glu, Gly. In another aspect, the variant comprises or consists of the substitution P152G, P152E, P152A of the polypeptide of SEQ ID NO: 1.

In another aspect, the variant comprises or consists of a substitution at a position corresponding to position 182. In another aspect, the amino acid at a position corresponding to position 182 is substituted with Ala, Arg, Asn, Asp, Cys, Gln, Glu, Gly, His, Ile, Leu, Lys, Met, Pro, Ser, Thr, Trp, Tyr, or Val, preferably with Val. In another aspect, the variant comprises or consists of the substitution F182V of the polypeptide of SEQ ID NO: 1.

In another aspect, the variant comprises or consists of a substitution at a position corresponding to position 185. In another aspect, the amino acid at a position corresponding to position 185 is substituted with Ala, Arg, Asn, Asp, Cys, Gln, Glu, Gly, His, Ile, Leu, Lys, Met, Pro, Ser, Thr, Trp, Tyr, or Val, preferably with Arg. In another aspect, the variant comprises or consists of the substitution F185R of the polypeptide of SEQ ID NO: 1.

In another aspect, the variant comprises or consists of a substitution at a position corresponding to position 583. In another aspect, the amino acid at a position corresponding to position 583 is substituted with Ala, Arg, Asn, Asp, Cys, Gln, Glu, His, Ile, Leu, Lys, Met, Phe, Pro, Ser, Thr, Trp, Tyr, or Val, preferably with Thr. In another aspect, the variant comprises or consists of the substitution G583T of the polypeptide of SEQ ID NO: 1.

In another aspect, the variant comprises or consists of substitutions at positions corresponding to positions 152 and 182, such as those described above.

In another aspect, the variant comprises or consists of substitutions at positions corresponding to positions 152 and 185, such as those described above.

In another aspect, the variant comprises or consists of substitutions at positions corresponding to positions 152 and 583, such as those described above.

In another aspect, the variant comprises or consists of substitutions at positions corresponding to positions 182 and 185, such as those described above.

In another aspect, the variant comprises or consists of substitutions at positions corresponding to positions 182 and 583, such as those described above.

In another aspect, the variant comprises or consists of substitutions at positions corresponding to positions 185 and 583, such as those described above.

In another aspect, the variant comprises or consists of substitutions at positions corresponding to positions 152, 182, and 185, such as those described above.

In another aspect, the variant comprises or consists of substitutions at positions corresponding to positions 152, 182, and 583, such as those described above.

In another aspect, the variant comprises or consists of substitutions at positions corresponding to positions 152, 185, and 583, such as those described above.

In another aspect, the variant comprises or consists of substitutions at positions corresponding to positions 182, 185, and 583, such as those described above.

In another aspect, the variant comprises or consists of substitutions at positions corresponding to positions 152, 182, 185, and 583, such as those described above.

In another aspect, the variant comprises or consists of one or more (e.g., several) substitutions selected from the group consisting of P152G, P152E, P152A, F182V, F185R, and G583T.

In another aspect, the variant comprises or consists of the substitutions P152G,E,A+F182V of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+F185R of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions F182V+F185R of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions F182V+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions F185R+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+F182V+F185R of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+F182V+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+F185R+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions F182V+F185R+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the variant comprises or consists of the substitutions P152G,E,A+F182V+F185R+G583T of the polypeptide of SEQ ID NO: 1, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has trehalase activity, and further the variant has increased stability against protease degradation and/or increased thermo-stability compared to the trehalase of SEQ ID NO: 1.

In another aspect, the trehalase variant polypeptide having increased stability against protease degradation, comprises a substitution or combination of substitutions selected from:
G583T;
P152G;
P152E;
P152A;
F182V;
F185R;
P152G+G583T;
F185R+G583T;
P152A+F182V+G583T;
F182V+F185R+G583T;
and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 3 and wherein the variant has trehalase activity and wherein the residual activity after 3 days incubation with *A. niger* protease mixture at 30° C., pH 4.0 is at least 50%, at least 60%, at least 70%, at least 80%.

In another aspect, the trehalase variant polypeptide having increased thermo-stability, comprises a substitution or combination of substitutions selected from:
P152G;
P152E;
P152A;
F182V;
F185R;
P152G+G583T;
F185R+G583T;
P152A+F182V+G583T;
F182V+F185R+G583T;

and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 3 and wherein the variant has trehalase activity and wherein the thermal denaturing temperature measure by TSA assay is at least 65.7° C.

In another aspect, the trehalase variant polypeptide having increased thermo-stability, comprises a substitution or combination of substitutions selected from:
P152G;
P152E;
P152A;
F182V;
F185R;
P152G+G583T;
F185R+G583T;
F182V+F185R+G583T;
and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 3 and wherein the variant has trehalase activity and wherein the thermal denaturing temperature measure by TSA assay is at least 65.8° C.

In another aspect, the trehalase variant polypeptide having increased thermo-stability, comprises a substitution or combination of substitutions selected from:
P152G;
P152E;
F182V;
F185R;
P152G+G583T;
F185R+G583T;
F182V+F185R+G583T;
and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 3 and wherein the variant has trehalase activity and wherein the thermal denaturing temperature measure by TSA assay is at least 66.0° C.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for trehalase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In an embodiment, the variant has increased stability against protease degradation compared to the parent enzyme.

In an embodiment, the variant has increased thermostability compared to the parent enzyme, e.g., SEQ ID NO: 1, as measured by TSA assay described herein. Particularly the thermal denaturing temperature, Td2, is at least 65.7° C., more particularly at least 65.8° C., more particularly 66.0° C.

Parent Trehalase

The parent trehalase may be (a) a polypeptide having at least 60% sequence identity to the polypeptide of SEQ ID NO: 1; (b) a polypeptide encoded by a polynucleotide that hybridizes under low stringency conditions with (i) the mature polypeptide coding sequence of SEQ ID NO: 2 or the cDNA thereof, or (iii) the full-length complement of (i) or (ii); or (c) a polypeptide encoded by a polynucleotide having at least 60% sequence identity to the mature polypeptide coding sequence of SEQ ID NO: 1.

The cDNA sequence is included herein as SEQ ID NO: 3.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the amino acid sequence of the parent differs by up to 10 amino acids, e.g., 1, 2, 3, 4, 5, 6, 7, 8, 9, or 10, from the polypeptide of SEQ ID NO: 1.

In another aspect, the parent comprises or consists of the amino acid sequence of SEQ ID NO: 1.

In another embodiment, the parent is an allelic variant of the polypeptide of SEQ ID NO: 1.

The polynucleotide of SEQ ID NO: 2 or a subsequence thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 2 or a subsequence thereof, the carrier material is used in a Southern blot.

For purposes of the present invention, hybridization indicates that the polynucleotide hybridizes to a labeled nucleic acid probe corresponding to (i) SEQ ID NO: 2; (ii) the mature polypeptide coding sequence of SEQ ID NO: 2; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 2. In another aspect, the nucleic acid probe is nucleotides 61 to 2022 of SEQ ID NO: 2. In another aspect, the nucleic acid probe is a polynucleotide that encodes the polypeptide of SEQ ID NO: 1; the mature polypeptide thereof; or a fragment thereof. In another aspect, the nucleic acid probe is SEQ ID NO: 2 or SEQ ID NO: 3.

In another embodiment, the parent is encoded by a polynucleotide having a sequence identity to the mature polypeptide coding sequence of SEQ ID NO: 2 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

In another aspect, the parent is a *Myceliophthora sepedonium* trehalase belonging to Family 37 Glucoside Hydrolases ("GH37") as defined by CAZY, e.g., the trehalase of SEQ ID NO: 1.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention. In one embodiment the polynucleotide is isolated.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. In one particular embodiment at least one control sequence is heterologous (of different origin/species) to the polynucleotide encoding the variant of the present invention.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. In a particular embodiment the recombinant host cell comprises the polynucleotide encoding a variant of the present invention in which the said polynucleotide is heterologous (of different origin/species) to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell. In a particular embodiment the host cell is a *Saccharomyces cerevisiae* cell. In a further particular embodiment, the host cell, particularly *Saccharomyces cerevisiae*, is used as fermenting organism expressing the trehalase according to the invention.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus,*

*Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. In a particular embodiment, the whole broth formulation is generated by fermentation of a recombinant host cell of the invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide having trehalase activity of the present invention. Preferably, the compositions are enriched in such a polypeptide. The term "enriched" indicates that the trehalase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In an embodiment the composition comprises a trehalase of the invention and a glucoamylase. In an embodiment the composition comprises a trehalase of the invention and a glucoamylase derived from *Talaromyces emersonii* (e.g., SEQ ID NO: 4). In an embodiment the composition comprises a trehalase of the invention and a glucoamylase derived from *Gloeophyllum*, such as *G. serpiarium* (e.g., SEQ ID NO: 5) or *G. trabeum* (e.g., SEQ ID NO: 6). In an embodiment, the composition comprises a trehalase of the invention, a glucoamylase and an alpha-amylase. In an embodiment, the composition comprises a trehalase of the invention, a glucoamylase and an alpha-amylase derived from *Rhizomucor*, preferably a strain the *Rhizomucor pusillus*, such as a *Rhizomucor pusillus* alpha-amylase hybrid having a linker (e.g., from *Aspergillus niger*) and starch-bonding domain (e.g., from *Aspergillus niger*). In an embodiment the composition comprises a trehalase of the invention, a glucoamylase, an alpha-amylase and a cellulolytic enzyme composition. In an embodiment, the composition comprises a trehalase of the invention, a glucoamylase, an alpha-amylase and a cellulolytic enzyme composition, wherein the cellulolytic composition is derived from *Trichoderma reesei*. In an embodiment the composition comprises a trehalase of the invention, a glucoamylase, an alpha-amylase and a protease. In an embodiment the composition comprises a trehalase of the invention, a glucoamylase, an alpha-amylase and a protease. The protease may be derived from *Thermoascus aurantiacus*. In an embodiment the composition comprises a trehalase of the invention, a glucoamylase, an alpha-amylase, a cellulolytic enzyme composition and a protease.

In an embodiment the composition comprises a trehalase of the invention, a glucoamylase, e.g., derived from *Talaromyces emersonii*, *Gloeophyllum serpiarium* or *Gloephyllum trabeum*, an alpha-amylase, e.g., derived from *Rhizomucor pusillus*, in particular one having a linker and starch-binding domain, in particular derived from *Aspergillus niger*, in particular one having the following substitutions: G128D+D143N (using SEQ ID NO: 7 for numbering); a cellulolytic enzyme composition derived from *Trichoderma reesei*, and a protease, e.g., derived from *Thermoascus aurantiacus* or *Meripilus giganteus*.

Examples of specifically contemplated secondary enzymes, e.g., a glucoamylase from *Talaromyces emersonii* shown in SEQ ID NO: 4 herein or a glucoamylase having, e.g., at least 60%, at least 70%, at least 80%, at least 90%, at least 95%, at least 96%, at least 97%, at least 98%, at least 99% identity to SEQ ID NO: 4 herein can be found in the "Enzymes" section below. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

Processes of the Invention

Producing a Fermentation Product from Gelatinized Starch Material Using a Trehalase of the Invention In this aspect the present invention relates to producing a fermentation product, in particular ethanol, from gelatinized and/or ungelatinized starch-containing material or cellulosic material. Fermentable sugars generated during saccharification/hydrolysis are converted to the desired fermentation in question, in particular ethanol, during fermentation by a fermenting organism, in particular yeast.

In an embodiment the invention relates to processes of producing a fermentation product, in particular ethanol, comprising
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of the invention;
iii) optionally a cellulolytic enzyme composition and/or a protease;
are present and/or added during
    saccharification step (b);
    fermentation step (c);
    simultaneous saccharification and fermentation;
    optionally presaccharification step before step (b).

In another embodiment the invention relates to processes of producing a fermentation product, in particular ethanol, comprising
(a) liquefying a starch-containing material with an alpha-amylase;
(b) saccharifying the liquefied material;
(c) fermenting using a fermentation organism;
wherein a glucoamylase and a trehalase of the invention are present and/or added during
    saccharification step (b);
    fermentation step (c);
    simultaneous saccharification and fermentation.

Liquefaction Step (a)

According to processes of the invention, liquefaction in step (a) is carried out by subjecting starch-containing material at a temperature above the initial gelatinization temperature, in particular at a temperature between 80-90° C., to an alpha-amylase and optionally a protease and other enzymes, such as a glucoamylase, a pullulanase and/or a phytase.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, Starch/Stärke 44(12): 461-466.

According to the invention liquefaction in step (a) is typically carried out at a temperature in the range from 70–100° C. In an embodiment the temperature in liquefaction is between 75-95° C., such as between 75-90° C., preferably between 80-90° C., such as 82-88° C., such as around 85° C.

The pH in liquefaction may be in the range between 3 and 7, preferably from 4 to 6, or more preferably from 4.5 to 5.5.

According to the invention a jet-cooking step may be carried out prior to liquefaction in step (a). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

In an embodiment, the process of the invention further comprises, prior to the liquefaction step (a), the steps of:
x) reducing the particle size of the starch-containing material, preferably by dry milling;
z) forming a slurry comprising the starch-containing material and water.

According to the invention the dry solid content (DS) in liquefaction lies in the range from 20-55 wt.-%, preferably 25-45 wt.-%, more preferably 30-40 wt.-% or 30-45 wt-%.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. According to the present invention dry milling is preferred.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

Liquefaction in step (a) may be carried out for 0.5-5 hours, such as 1-3 hours, such as typically around 2 hours.

The alpha-amylase and other optional enzymes, such as protease, may initially be added to the aqueous slurry to initiate liquefaction (thinning). In an embodiment only a portion of the enzymes (e.g., about ⅓) is added to the aqueous slurry, while the rest of the enzymes (e.g., about ⅔) are added in liquefaction step (a).

A non-exhaustive list of examples of alpha-amylases can be found below in the "Alpha-Amylase Present and/or Added In Liquefaction"-section. In a preferred embodiment the alpha-amylase is a bacterial alpha-amylase. Bacterial alpha-amylases are typically thermostable. In a preferred embodiment the alpha-amylase is derived from the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 8 herein.

In an embodiment the alpha-amylase used in liquefaction step (a) is a variant of the Bacillus stearothermophilus alpha-amylase shown in SEQ ID NO: 8 herein, in particular with the double deletions in I181*+G182*, and optionally with a N193F substitution, and truncated to be around 491 amino acids long, e.g., from 480-495 amino acids long.

Examples of suitable Bacillus stearothermophilus alpha-amylase variants can be found below in the "Thermostable Alpha-Amylase"-section and include one from the following group of Bacillus stearothermophilus alpha-amylase variants with double deletions I181*+G182*, and optionally substitution N193F, and additionally the following substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S
      (using SEQ ID NO: 8 for numbering).

According to processes of the invention, liquefaction in step (a) may be carried out using a combination of alpha-amylase (e.g., Bacillus stearothermophilus alpha-amylase shown in SEQ ID NO: 8) and protease (e.g., Pyrococcus furiosus (pfu protease) shown in SEQ ID NO: 9). A glucoamylase may also be present, such as the one derived from Penicillium oxalicum shown in SEQ ID NO: 10 herein (see the "Glucoamylase Present and/or Added In Liquefaction Step (a)"-section below.

Saccharification and Fermentation

A trehalase of the invention, a glucoamylase and optionally a protease and/or a cellulolytic enzyme composition may be present and/or added in saccharification step (b); fermentation step (c); simultaneous saccharification and fermentation (SSF); optionally a presaccharification step before step (b).

In a preferred embodiment, the glucoamylase is added together with a fungal alpha-amylase, in particular acid fungal alpha-amylase. Examples of glucoamylases can be found in the "Glucoamylases Present and/or Added In Saccharification and/or Fermentation"-section below. When doing sequential saccharification and fermentation, saccharification step (b) may be carried out at conditions well-known in the art, i.e., suitable for enzyme saccharification. For instance, the saccharification step (b) may last up to from about 24 to about 72 hours.

In an embodiment, pre-saccharification is done before saccharification in step (b). Pre-saccharification is typically done for 40-90 minutes at a temperature between 30-65° C., typically about 60° C. Pre-saccharification is in an embodiment followed by saccharification during fermentation in simultaneous saccharification and fermentation (SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step (b) and the fermentation step (c) are carried out simultaneously. There is no holding stage for the saccharification, meaning that a fermenting organism, in particular yeast, and enzymes, may be added together. However, it is also contemplated to add the fermenting organism and enzymes separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 4-5.

In an embodiment of the invention a cellulolytic composition is present and/or added in saccharification step (b), fermentation step (c) or simultaneous saccharification and fermentation (SSF) or pre-saccharification before step (b). Examples of such cellulolytic compositions can be found in the "Cellulolytic Enzyme Composition present and/or added during Saccharification and/or Fermentation"-section below. The optional cellulolytic enzyme composition may be present and/or added together with the glucoamylase and trehalase of the invention. Examples of proteases can be found in the "Proteases Present and/or Added In Saccharification and/or Fermentation"-section below.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

Starch-Containing Materials

According to the invention any suitable starch-containing starting material may be used. The starting material is generally selected based on the desired fermentation product, in particular ethanol. Examples of starch-containing starting materials, suitable for use in processes of the present invention, include cereal, tubers or grains. Specifically the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Producing a Fermentation Product from Ungelatinized Starch Material Using a Trehalase of the Invention A trehalase of the invention may suitably be used in a raw starch hydrolysis (RSH) process for producing desired fermentation products, in particular ethanol. In RSH processes the starch does not gelatinize as the process is carried out at temperatures below the initial gelatinization temperature of the starch in question (defined above).

The desired fermentation product may in an embodiment be ethanol produced from un-gelatinized (i.e., uncooked), preferably milled, grains, such as corn, or small grains such as wheat, oats, barley, rye, rice, or cereals such as sorghum. Examples of suitable starch-containing starting materials are listed in the section "Starch-Containing Materials"-section above.

Accordingly, in this aspect the invention relates to processes of producing fermentation products from starch-containing material comprising:

(a) saccharifying a starch-containing material at a temperature below the initial gelatinization temperature; and
(b) fermenting using a fermentation organism; and
(c) optionally recovering the fermentation product;

wherein saccharification and/or fermentation is done in the presence of the following enzymes: glucoamylase, alpha-amylase, trehalase of the invention, and optionally a cellulolytic enzyme composition and/or a protease.

Before step (a) an aqueous slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. Because a raw starch hydrolysis process of the invention is carried out below the initial gelatinization temperature, and thus no significant viscosity increase takes place, high levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

A RSH process of the invention is conducted at a temperature below the initial gelatinization temperature, which means that the temperature at which a separate step (a) is carried out typically lies in the range between 25–75° C., such as between 30-70° C., or between 45-60° C.

In a preferred embodiment the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

In an embodiment of the invention fermentation is carried out for 30 to 150 hours, preferably 48 to 96 hours. 66.

In an embodiment fermentation is carried out so that the sugar level, such as glucose level, is kept at a low level, such as below 6 wt.-%, such as below about 3 wt.-%, such as below about 2 wt.-%, such as below about 1 wt.-%, such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 and WO2004/081193 (both references are incorporated by reference). Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

According to the invention the enzymes are added so that the glucoamylase is present in an amount of 0.001 to 10 AGU/g DS, preferably from 0.01 to 5 AGU/g DS, especially 0.1 to 0.5 AGU/g DS.

According to the invention the enzymes are added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes are added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes are added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes are added so that the protease is present in an amount of 0.0001-1 mg enzyme protein per g DS, preferably 0.001 to 0.1 mg enzyme protein per g DS. Alternatively, the protease is present and/or added in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes are added so that the protease is present or added in an amount in the range 1-1,000 µg EP/g DS, such as 2-500 µg EP/g DS, such as 3-250 µg EP/g DS.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is according to the invention from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the glucoamylase, such as one derived from *Trametes cingulata*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 11.

In an embodiment the glucoamylase, such as one derived from *Pycnoporus sanguineus*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12.

In an embodiment the alpha-amylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 7.

In a preferred embodiment the invention relates to processes of producing fermentation products from starch-containing material comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase;
  ii) alpha-amylase;
  iii) trehalase of the invention;
  iii) optionally a cellulolytic enzyme composition and/or a protease.

In a preferred embodiment the enzymes may be added as an enzyme composition of the invention. In a preferred embodiment steps (a) and (b) are carried out simultaneously (i.e., one-step fermentation). However, step (a) and (b) may also be carried our sequentially.

Fermentation

Fermentation is carried out in a fermentation medium. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms for Starch Based Fermentation

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as in particular ethanol. Examples of fermenting organisms include fungal organisms, such as in particular yeast. Preferred yeast includes strains of *Saccharomyces* spp., in particular, *Saccharomyces cerevisiae*. In a particular embodiment the variant trehalase is coformulated with the fermenting organism, particularly a yeast organism, more particularly a dry yeast.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about 5×10'.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Recovery

Subsequent to fermentation, e.g., SSF, the fermentation product, in particular ethanol may be separated from the fermentation medium. The slurry may be distilled to recover/extract the desired fermentation product (i.e., ethanol). Alternatively the desired fermentation product (i.e., ethanol) may be extracted from the fermentation medium by micro or membrane filtration techniques. The fermentation product (i.e., ethanol) may also be recovered by stripping or other method well known in the art.

Alpha-Amylase Present and/or Added in Liquefaction

According to the invention an alpha-amylase is present and/or added in liquefaction optionally together with other enzymes such as a protease, a glucoamylase, phytase and/or pullulanase. The alpha-amylase added in liquefaction step (a) may be any alpha-amylase. Preferred are bacterial alpha-amylases, which typically are stable at temperatures used in liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens*, *Bacillus licheniformis*, *Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 8 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 8 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids, e.g., so that it is between 480-495 amino acids long, so it lacks a functional starch binding domain (compared to SEQ ID NO: 3 in WO 99/19467) or SEQ ID NO: 8 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 8 herein or the deletion of amino acids R179 and G180 using SEQ ID NO: 3 in WO 99/19467 or SEQ ID NO: 8 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 8 herein. The bacterial alpha-amylase may also have a substitution in a position corresponding to S239 in the *Bacillus licheniformis* alpha-amylase shown in SEQ ID NO: 4 in WO 99/19467, or a S242 and/or E188P variant of the *Bacillus stearothermophilus* alpha-amylase of SEQ ID NO: 3 in WO 99/19467 or SEQ ID NO: 8 herein. In an embodiment the variant is a S242A, E or Q variant, preferably a S242Q variant, of the *Bacillus stearothermophilus* alpha-amylase (using SEQ ID NO: 8 herein for numbering).

In an embodiment the variant is a position E188 variant, preferably E188P variant of the *Bacillus stearothermophilus* alpha-amylase (using SEQ ID NO: 8 herein for numbering).

The bacterial alpha-amylase may in an embodiment be a truncated *Bacillus* alpha-amylase. Especially the truncation is so that, e.g., the *Bacillus stearothermophilus* alpha-amylase shown in SEQ ID NO: 3 in WO 99/19467 or SEQ ID NO: 8 herein, is around 491 amino acids long, such as from 480 to 495 amino acids long, or so it lack a functional starch binding domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:
G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

The alpha-amylase may be a thermostable alpha-amylase, such as a thermostable bacterial alpha-amylase, preferably from *Bacillus stearothermophilus*.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 8 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optionally substitution N193F, further comprising mutations selected from below list:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91L+M96I+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V.
V59A+E129V+K177L+R179E+Q254S+M284V;

Specific information about the thermostability of above alpha-amylases variants can be found in WO12/088303 (Novozymes) which is hereby incorporated by reference.

In a preferred embodiment the alpha-amylase is selected from the group of *Bacillus stearothermophilus* alpha-amylase variants having a double deletion in I181+G182, and optionally a substitution in N193F, and substitutions from the following list
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 8 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 8 herein, or variants thereof, are truncated in the C-terminal and are typically around 491 amino acids long, such as from 480-495 amino acids long, or so that it lacks a functional starch binding domain.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 8 herein.

In an embodiment the bacterial alpha-amylase, e.g., *Bacillus* alpha-amylase, such as especially *Bacillus stearothermophilus* alpha-amylase, or variant thereof, is dosed to liquefaction in a concentration between 0.01-10 KNU-Ng DS, e.g., between 0.02 and 5 KNU-Ng DS, such as 0.03 and 3 KNU-A, preferably 0.04 and 2 KNU-Ng DS, such as especially 0.01 and 2 KNU-Ng DS. In an embodiment the bacterial alpha-amylase, e.g., *Bacillus* alpha-amylase, such as especially *Bacillus stearothermophilus* alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

Protease Present and/or Added in Liquefaction

According to the invention a protease may optionally be present and/or added in liquefaction together with the alpha-amylase, and an optional glucoamylase, phytase and/or pullulanase. Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein).

Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

In one embodiment the protease is of fungal origin.

The protease may be a variant of, e.g., a wild-type protease as long as the protease is thermostable. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39). In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 13 herein, further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

Specific information about the thermostability of above protease variants can be found in WO12/088303 (Novozymes), which is hereby incorporated by reference.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 13 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 13 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), or SEQ ID NO: 9 herein.

In another embodiment the thermostable protease is one disclosed in SEQ ID NO: 9 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 9 herein. *Pyroccus furiosus* protease can be purchased from Takara Bio, Japan.

Glucoamylase Present and/or Added in Liquefaction

According to the invention a glucoamylase may optionally be present and/or added in liquefaction step (a). In a preferred embodiment the glucoamylase is added together with or separately from the alpha-amylase and optional protease, phytase and/or pullulanase.

In a specific and preferred embodiment the glucoamylase, preferably of fungal origin, preferably a filamentous fungi, is from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 10 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 10 herein.

In a preferred embodiment the glucoamylase is a variant of the *Penicillium oxalicum* glucoamylase disclosed as SEQ ID NO: 2 in WO 2011/127802 and shown in SEQ ID NO: 10 herein, having a K79V substitution (using the mature sequence shown in SEQ ID NO: 10 herein for numbering).

The K79V glucoamylase variant has reduced sensitivity to protease degradation relative to the parent as disclosed in WO 2013/036526 (which is hereby incorporated by reference). In an embodiment the glucoamylase is derived from *Penicillium oxalicum*.

In an embodiment the glucoamylase is a variant of the *Penicillium oxalicum* glucoamylase disclosed as SEQ ID NO: 2 in WO 2011/127802 and shown in SEQ ID NO: 10 herein. In a preferred embodiment the *Penicillium oxalicum* glucoamylase is the one disclosed as SEQ ID NO: 2 in WO 2011/127802 and shown in SEQ ID NO: 10 herein having Val (V) in position 79 (using SEQ ID NO: 10 herein for numbering).

Contemplated *Penicillium oxalicum* glucoamylase variants are disclosed in WO 2013/053801 which is hereby incorporated by reference.

In an embodiment these variants have reduced sensitivity to protease degradation.

In an embodiment these variant have improved thermostability compared to the parent.

More specifically, in an embodiment the glucoamylase has a K79V substitution (using SEQ ID NO: 10 herein for numbering), (PE001 variant), and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or

P2N+P4S+P11F+T65A+I172V+Q327F+E501V+Y504T; or

P2N+P4S+P11F+T65A+Q327F+S377T+E501V+Y504T; or

P2N+P4S+P11F+D26N+K34Y+T65A+Q327F; or
P2N+P4S+P11F+T65A+Q327F+I375A+E501V+Y504T; or

P2N+P4S+P11F+T65A+K218A+K221D+Q327F+E501V+Y504T; or

P2N+P4S+P11F+T65A+S103N+Q327F+E501V+Y504T; or

P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or

P2N+T10E+E18N+T65A+Q327F+E501V+Y504T; or
P2N+P4S+P11F+T65A+Q327F+E501V+Y504T+T568N; or

P2N+P4S+P11F+T65A+Q327F+E501V+Y504T+K524T+G526A; or

P2N+P4S+P11F+K34Y+T65A+Q327F+D445N+V447S+E501V+Y504T; or

P2N+P4S+P11F+R31S+K33V+T65A+Q327F+D445N+V447S+E501V+Y504T; or

P2N+P4S+P11F+D26N+K34Y+T65A+Q327F+E501V+Y504T; or

P2N+P4S+P11F+T65A+F80*+Q327F+E501V+Y504T; or

P2N+P4S+P11F+T65A+K112S+Q327F+E501V+Y504T; or

P2N+P4S+P11F+T65A+Q327F+E501V+Y504T+T516P+K524T+G526A; or

P2N+P4S+P11F+T65A+Q327F+E501V+N502T+Y504*; or

P2N+P4S+P11F+T65A+Q327F+E501V+Y504T; or
P2N+P4S+P11F+T65A+S103N+Q327F+E501V+Y504T; or

K5A+P11F+T65A+Q327F+E501V+Y504T; or
P2N+P4S+P11F+T65A+Q327F+E501V+Y504T+T516P+K524T+G526A; or

P2N+P4S+P11F+T65A+V79A+Q327F+E501V+Y504T; or

P2N+P4S+P11F+T65A+V79G+Q327F+E501V+Y504T; or

P2N+P4S+P11F+T65A+V79I+Q327F+E501V+Y504T; or

P2N+P4S+P11F+T65A+V79L+Q327F+E501V+Y504T; or

P2N+P4S+P11F+T65A+V79S+Q327F+E501V+Y504T; or

P2N+P4S+P11F+T65A+L72V+Q327F+E501V+Y504T; or

S255N+Q327F+E501V+Y504T; or
P2N+P4S+P11F+T65A+E74N+V79K+Q327F+E501V+Y504T; or

P2N+P4S+P11F+T65A+G220N+Q327F+E501V+Y504T; or

P2N+P4S+P11F+T65A+Y245N+Q327F+E501V+Y504T; or

P2N+P4S+P11F+T65A+Q253N+Q327F+E501V+Y504T; or

P2N+P4S+P11F+T65A+D279N+Q327F+E501V+Y504T; or

P2N+P4S+P11F+T65A+Q327F+S359N+E501V+Y504T; or

P2N+P4S+P11F+T65A+Q327F+D370N+E501V+Y504T; or

P2N+P4S+P11F+T65A+Q327F+V460S+E501V+Y504T; or

P2N+P4S+P11F+T65A+Q327F+V460T+P468T+E501V+Y504T; or

P2N+P4S+P11F+T65A+Q327F+T463N+E501V+Y504T; or

P2N+P4S+P11F+T65A+Q327F+S465N+E501V+Y504T; or

P2N+P4S+P11F+T65A+Q327F+T477N+E501V+Y504T.

In a preferred embodiment the *Penicillium oxalicum* glucoamylase variant has a K79V substitution (using SEQ ID NO: 10 herein for numbering), corresponding to the PE001 variant, and further comprises one of the following mutations:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Trehalase Present and/or Added in Saccharification and/or Fermentation

According to the process of the invention a trehalase of the invention is present and/or added during the
saccharification step (b);
fermentation step (c);
simultaneous saccharification and fermentation;
optionally presaccharification step before step (b).

In a preferred embodiment the trehalase is present and/or added in an amount between 0.01-20 ug EP (Enzyme Protein) trehalase/g DS, such as between 0.05-15 ug EP terhalase/g DS, such as between 0.5 and 10 ug EP trehalase/g DS.

Glucoamylase Present and/or Added in Saccharification and/or Fermentation

The glucoamylase present and/or added_during saccharification step (b); fermentation step (c); simultaneous saccharification and fermentation; or presaccharification before step (b), may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from

*Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831). Contemplated fungal glucoamylases include *Trametes cingulate* (SEQ ID NO: 11), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus sanguineus* as described in WO 2011/066576 (SEQ ID NOs 2, 4 or 6), in particular the one shown a SEQ ID NO: 12 herein (corresponding to SEQ ID NO: 4 in WO 2011/066576) or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 5 herein (i.e. *Gloeophyllum sepiarium* glucoamylase). In a preferred embodiment the glucoamylase is SEQ ID NO: 6 herein (i.e., *Gloeophyllum trabeum* glucoamylase discloses as SEQ ID NO: 3 in WO2014/177546) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 4, 11, 5, 6 or 12 herein, respectively.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 6 herein.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may in an embodiment be added to the saccharification and/or fermentation in an amount of 1-1,000 μg EP/g DS, preferably 10-500 μg/gDS, especially between 25-250 μg/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 34 or SEQ ID NO: 4 herein and *Trametes cingulata* glucoamylase disclosed as SEQ ID NO: 2 in WO 06/069289 and SEQ ID NO: 11 herein.

In an embodiment the glucoamylase is a blend comprising *Talaromyces emersonii* glucoamylase disclosed in SEQ ID NO: 4 herein, *Trametes cingulata* glucoamylase disclosed as SEQ ID NO: 11 herein, and *Rhizomucor pusillus* alpha-amylase with *Aspergillus niger* glucoamylase linker and SBD disclosed as V039 in Table 5 in WO 2006/069290 or SEQ ID NO: 7 herein.

In an embodiment the glucoamylase is a blend comprising *Gloeophyllum sepiarium* glucoamylase shown as SEQ ID NO: 5 herein and *Rhizomucor pusillus* with an *Aspergillus niger* glucoamylase linker and starch-binding domain (SBD), disclosed SEQ ID NO: 7 herein with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 7 herein.

In an embodiment the *Rhizomucor pusillus* alpha-amylase or the *Rhizomucor pusillus* alpha-amylase with a linker and starch-binding domain (SBD), preferably *Aspergillus niger* glucoamylase linker and SBD, has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering or SEQ ID NO: 7 herein). In a preferred embodiment the glucoamylase blend comprises *Gloeophyllum sepiarium* glucoamylase (e.g., SEQ ID NO: 2 in WO 2011/068803 or SEQ ID NO: 5 herein) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 or SEQ ID NO: 5 herein and *Rhizomucor pusillus* with a linker and starch-binding domain (SBD), preferably *Aspergillus niger* glucoamylase linker and SBD, disclosed SEQ ID NO: 3 in WO 2013/006756 and SEQ ID NO: 7 herein with the following substitutions: G128D+D143N.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™, and AMG™ E (from Novozymes NS); OPTIDEX™ 300, GC480, GC417 (from DuPont-Danisco); AMI- GASE™ and AMIGASE™ PLUS (from DSM); G-ZYME™ G900, G-ZYME™ and G990 ZR (from DuPont-Danisco).

Cellulolytic Enzyme Composition Present and/or Added in Saccharification and/or Fermentation According to the invention a cellulolytic enzyme composition may be present in saccharification, fermentation or simultaneous saccharification and fermentation (SSF).

The cellulolytic enzyme composition comprises a beta-glucosidase, a cellobiohydrolase and an endoglucanase.

Examples of suitable cellulolytic composition can be found in WO 2008/151079 and WO 2013/028928 which are incorporated by reference.

In preferred embodiments the cellulolytic enzyme composition is derived from a strain of *Trichoderma, Humicola,* or *Chrysosporium*.

In an embodiment the cellulolytic enzyme composition is derived from a strain of *Trichoderma reesei, Humicola insolens* and/or *Chrysosporium lucknowense*.

In an embodiment the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (in particular the *Aspergillus oryzae* beta-glucosidase variant fusion protein shown in SEQ ID NOs: 73 and 74, respectively, in WO 2008/057637 or the *Aspergillus oryzae* beta-glucosidase fusion protein shown in SEQ ID NOs: 75 and 76, respectively, in WO 2008/057637—both hereby incorporated by reference), or *Aspergillus fumigatus*, such as one disclosed in WO 2005/047499 or SEQ ID NO: 14 herein or an *Aspergillus fumigatus* beta-glucosidase variant disclosed in WO 2012/044915 (Novozymes), such as one with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 2 in WO 2011/057140 or SEQ ID NO: 17 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* disclosed as SEQ ID NO: 18 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the cellulolytic enzyme composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499 or SEQ ID NO: 14 herein).

In an embodiment the cellulolytic enzyme composition is a *Trichoderma reesei* cellulolytic enzyme composition further comprising *Penicillium emersonii* GH61A polypeptide having cellulolytic enhancing activity disclosed as SEQ ID NO: 2 in WO 2011/041397 or SEQ ID NO: 16 herein and *Aspergillus fumigatus* beta-glucosidase (SEQ ID NO: 2 of WO 2005/047499 or SEQ ID NO: 14 herein) or a variant thereof with the following substitutions F100D, S283G, N456E, F512Y (using SEQ ID NO: 14 herein for numbering).

In a preferred embodiment the cellulolytic enzyme composition comprising one or more of the following components:

(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In an preferred embodiment the cellulolytic enzyme composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 16 herein), *Aspergillus fumigatus* beta-glucosidase (SEQ ID NO: 2 in WO 2005/047499 or SEQ ID NO: 14 herein) variant with the following substitutions: F100D, S283G, N456E, F512Y (disclosed in WO 2012/044915); *Aspergillus fumigatus* Cel7A CBH I disclosed as SEQ ID NO: 6 in WO2011/057140 or SEQ ID NO: 6 herein and *Aspergillus fumigatus* CBH II disclosed as SEQ ID NO: 17 in WO 2011/057140 or SEQ ID NO: 18 herein.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Proteases Present and/or Added in Saccharification and/or Fermentation

Any suitable protease may be added in saccharification and/or fermentation, such as SSF. In a preferred embodiment the protease is a metallo protease or a serine protease. In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 13 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 13 herein.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 9 herein.

In an embodiment the protease is the mature sequence from *Meripilus giganteus* protease 3 (peptidase family S53 protease) concerned in Example 2 in WO 2014/037438 (hereby incorporated by reference). In an embodiment the protease is the mature protease 3 sequence from a strain of *Meripilus*, in particular *Meripilus giganteus* shown as SEQ ID NO: 5 in WO 2014/037438 (hereby incorporated by reference) and SEQ ID NO: 19 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 19 herein shown as amino acids 1-547.

Alpha-Amylase Present and/or Added in Saccharification and/or Fermentation

Any suitable alpha-amylase, such as fungal acid alpha-amylase, may be present and/or added in saccharification and/or fermentation.

In a preferably embodiment the alpha-amylase is a fungal alpha-amylase, in particular one that has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 7. In a preferred embodiment the alpha-amylase has one or more of the following substitutions: G128D, D143N, in particular G128D+D143N.

Processes of Producing a Fermentation Product from Cellulolic Materials Using a Trehalase of the Invention In an embodiment the invention relates to processes of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product,
wherein a trehalase of the invention is added and/or present in hydrolysis step (a) and/or fermentation step (b).

According to the process of the invention hydrolysis and fermentation may be carried out separate or simultaneous. In an embodiment the process of the invention is carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); or direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step. SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in a HHF process can be carried out at different temperatures, i.e., high temperature enzymatic hydrolysis followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product.

According to the invention the cellulosic material is plant material chips, plant stem segments and/or whole plant stems. In an embodiment cellulosic material is selected from the group comprising arundo, bagasse, bamboo, corn cob, corn fiber, corn stover, miscanthus, orange peel, rice straw, switchgrass, wheat straw. In a preferred embodiment the source of the cellulosic material is corn stover, corn cobs, and/or wheat straw.

According to the invention any pretreatment may be used. In a preferred embodiment chemical pretreatment, physical pretreatment, or chemical pretreatment and a physical pretreatment is used. In a preferred embodiment the cellulosic material is pretreated with an acid, such as dilute acid pretreatment. In an embodiment the cellulosic material is prepared by pretreating cellulosic material at high temperature, high pressure with an acid.

In an embodiment hydrolysis is carried out at a temperature between 20-70° C., such as 30-60° C., preferably 45-55° C. at a pH in the range 4-6, such as 4.5-5.5.

In an embodiment the cellulosic material is present at 1-20 (w/w) % of TS, such as 2-10 (w/w) % TS, such as around 5 (w/w) % TS during hydrolysis.

In an embodiment the hydrolysis is carried out for 1-20 days, preferably between from 5-15 days.

In an embodiment the cellulolytic enzyme composition is derived from *Trichoderma reesei*, *Humicola insolens* or *Chrysosporium lucknowense*.

Cellulolytic enzyme composition: The term "cellulolytic enzyme composition" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Examples of cellulolytic compositions can be found in the "Cellulolytic Enzyme Composition present and/or added during Saccharification and/or Fermentation"-section above.

Cellulosic material: The term "cellulosic material" means any material containing cellulose. The predominant polysaccharide in the primary cell wall of cellulosic material is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, Trends in Biotechnology 15: 160-167; Teeri et al., 1998, Trichoderma reesei cellobiohydrolases: why so efficient on crystalline cellulose?, Biochem. Soc. Trans. 26: 173-178). Cellobiohydrolase activity is determined according to the procedures described by Lever et al., 1972, Anal. Biochem. 47: 273-279; van Tilbeurgh et al., 1982, FEBS Letters 149: 152-156; van Tilbeurgh and Claeyssens, 1985, FEBS Letters 187: 283-288; and Tomme et al., 1988, Eur. J. Biochem. 170: 575-581. In the present invention, the Tomme et al. method can be used to determine cellobiohydrolase activity.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, Biotechnology Advances 24: 452-481). For purposes of the present invention, endoglucanase activity is determined using carboxymethyl cellulose (CMC) as substrate according to the procedure of Ghose, 1987, Pure and Appl. Chem. 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, Biochem. J. 280: 309-316, and Henrissat and Bairoch, 1996, Updating the sequence-based classification of glycosyl hydrolases, Biochem. J. 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of cellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. Current Opinion In Microbiology 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature, e.g., 50° C., 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5L (Novozymes A/S, Bagsvrd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Fermenting Organism for Cellulosic Based Fermentation

The term "fermenting organism" or "fermenting microorganism" refers to any organism, including bacterial and fungal organisms, suitable for use in a desired fermentation process to produce a fermentation product. The fermenting organism may be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting organisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the term "fermentation product" can be any substance derived from fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, Miya, and Kiriyama, 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy,* 13(1-2): 83-114.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

Recovery

The fermentation product(s) are optionally recovered after fermentation using any method known in the art including, but not limited to, chromatography, electrophoretic procedures, differential solubility, distillation, or extraction. For example, alcohol, such as ethanol, is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further disclosed in the following numbered embodiments:

Embodiment 1. A trehalase variant polypeptide having increased stability against protease degradation and/or increased thermo-stability, comprising a substitution at one or more positions corresponding to position 152, 182, 185, or 583 of SEQ ID NO: 1, wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity.

Embodiment 2. The variant of embodiment 1, wherein the number of substitutions are 1-20, e.g., 1-10 and 1-5, such as 1, 2, 3, 4, 5, 6, 7, 8, 9 or 10 substitutions.

Embodiment 3. The variant of any of embodiments 1-2, which comprises a substitution at a position corresponding to position P152.

Embodiment 4. The variant of embodiment 3, wherein the substitution is a substitution with Gly, Glu, or Ala.

Embodiment 5. The variant of any of embodiments 1-4, which comprises a substitution at a position corresponding to position F182.

Embodiment 6. The variant of embodiment 5, wherein the substitution is a substitution with Val.

Embodiment 7. The variant of any of embodiments 1-6, which comprises a substitution at a position corresponding to position F185.

Embodiment 8. The variant of embodiment 7, wherein the substitution is a substitution with Arg.

Embodiment 9. The variant of any of embodiments 1-8, which comprises a substitution at a position corresponding to position G583.

Embodiment 10. The variant of embodiment 9, wherein the substitution is a substitution with Thr.

Embodiment 11. The variant of any of embodiments 1-10, which comprises a substitution at two positions corresponding to any of positions 152, 182, 185, or 583.

Embodiment 12. The variant of any of embodiments 1-10, which comprises a substitution at three positions corresponding to any of positions 152, 182, 185, or 583.

Embodiment 13. The variant of any of embodiments 1-10, which comprises a substitution at each position corresponding to positions 152, 182, 185, or 583.

Embodiment 14. The variant of any of embodiments 1-13, which comprises one or more substitutions selected from the group consisting of P152G, P152E, P152A, F182V, F185R, or G583T.

Embodiment 15. The variant of any of embodiments 1-14 having an increase in stability against protease degradation, comprising a substitution or combination of substitutions selected from:

G583T;
P152G;
P152E;
P152A;
F182V;
F185R;
P152G+G583T;
F185R+G583T;
P152A+F182V+G583T;
F182V+F185R+G583T;

and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity and wherein the residual activity after 3 days incubation with *A. niger* protease mixture at 30° C., pH 4.0 is at least 50%, at least 60%, at least 70%, at least 80%.

Embodiment 16. The variant of any of embodiments 1-14 having an increase in thermo-stability, comprising a substitution or combination of substitutions selected from:
P152G;
P152E;
P152A;
F182V;
F185R;
P152G+G583T;
F185R+G583T;
P152A+F182V+G583T;
F182V+F185R+G583T;
and wherein the variant has at least 75%, at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity and wherein the thermal denaturing temperature measure by TSA assay is at least 65.7° C.

Embodiment 17. The variant of embodiment 16, wherein the thermal denaturing temperature is at least 65.8° C., at least 65.9° C., at least 66.0° C., at least 66.1° C., at least 66.2° C., at least 66.3° C., at least 66.4° C., at least 66.5° C., at least 66.6° C., at least 66.6° C., at least 66.8° C., at least 66.9° C., at least 67.0° C., at least 67.1° C., at least 67.2° C., at least 67.3° C., at least 67.4° C., at least 67.5° C.

Embodiment 18. An polynucleotide encoding the variant of any of embodiments 1-17. Embodiment 19. A nucleic acid construct comprising the polynucleotide of embodiment 18.

Embodiment 20. An expression vector comprising the polynucleotide of embodiment 18.

Embodiment 21. A host cell comprising the polynucleotide of embodiment 18 or the nucleic acid construct of embodiment 19.

Embodiment 22. The host cell of embodiment 21, selected from a yeast host cell, particularly a *Saccharomyces* sp., more particularly a *Saccharomyces cerevisiae*.

Embodiment 23. A composition comprising the polypeptide of any of embodiments 1-17.

Embodiment 24. A whole broth formulation or cell culture composition comprising the polypeptide of embodiment 1-17.

Embodiment 25. A method of producing a trehalase variant, comprising:
cultivating the host cell of embodiment 21 under conditions suitable for expression of the variant;
and recovering the variant.

Embodiment 26. The method of embodiment 25, wherein the host cell is a yeast host cell, particularly a yeast selected from the group consisting of: *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell, most particularly *Saccharomyces cerevisiae*.

Embodiment 27. A process of producing a fermentation product, comprising
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of embodiment 1;
iii) optionally a cellulolytic enzyme composition and/or a protease;
are present and/or added during
saccharification step (b);
fermentation step (c);
simultaneous saccharification and fermentation;
optionally presaccharification step before step (b).

Embodiment 28. A process of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase, alpha-amylase, variant trehalase of embodiment 1, and optionally a protease and/or a cellulolytic enzyme composition.

Embodiment 29. A process of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product,
wherein a variant trehalase of embodiment 1 is added and/or present in hydrolysis step (a) and/or fermentation step (b).

Embodiment 30. The process according to any of embodiments 27-29, wherein the fermenting organism is the host cell according to any of embodiments 21, particularly a yeast host cell, particularly a yeast selected from the group consisting of: *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell, most particularly *Saccharomyces cerevisiae*.

Embodiment 31. The process according to any of embodiments 27-29, wherein the variant trehalase is coformulated with the fermenting organism, particularly a yeast organism, more particularly a dry yeast.

Embodiment 32. The process of any of embodiments 27-31, wherein the fermentation product is an alcohol, particularly ethanol.

The present invention is further described by the following examples.

EXAMPLES

Materials & Methods
Trehalase Assay:
Principle:

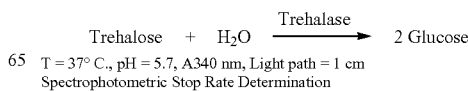

$T = 37° C., pH = 5.7, A340\ nm, Light\ path = 1\ cm$
Spectrophotometric Stop Rate Determination Unit Definition:

One unit will convert 1.0 mmole of trehalose to 2.0 mmoles of glucose per minute at pH 5.7 at 37° C. (liberated glucose determined at pH 7.5).

(See Dahlqvist, A. (1968) Analytical Biochemistry 22, 99-107)

Example 1

Positions suitable for improving thermo-stability and protease stability of the wild type *Myceliophthora sepedonium* GH37 trehalase were identified and specific variants were constructed. The specific single substitution variants and combinations thereof were tested for increase in thermal denaturation temperature, Td, determined by thermal shift assay (TSA), and increase in residual activity after 3 days incubation in presence of a protease mixture at three different temperatures as a measure of increased stability towards protease degradation (protease stability assay). The specific variants constructed and tested are shown in Table 1 and the resulting increase in melting temperature and protease stability is shown in Table 2.

TABLE 1

M-trehalase PE variants

| Variants | Substitutions |
|---|---|
| JTH001 | G583T |
| JTH061 | P152G |
| JTH062 | P152E |
| JTH063 | P152A |
| JTH064 | F182V |
| JTH065 | F185R |
| JTH066 | P152G G583T |
| JTH067 | F185R G583T |
| JTH076 | P152A F182V G583T |
| JTH078 | F182V F185R G583T |

Purification

Purification of wild type trehalases and trehalase variants were carried out by two steps, desalting column and cation exchange chromatography column. Finally, the samples were dialyzed against 10 L of 20 mM sodium acetate buffer (pH 4.0) using 12 k-14 k MWCO (molecular weight-cutoff) dialysis membrane and then concentrated using 30 k MWCO centrifugal filter unit.

Thermostability Determination (TSA)

Purified enzyme was diluted to 0.5 mg/ml with 50 mM sodium acetate buffer (pH 4.5) and mixed with equal volume of SYPRO Orange (Invitrogen) diluted with Milli-Q water. Eighteen microliters of mixture solution was transfer to LightCycler 480 Multiwell Plate 384 (Roche Diagnostics) and the plate was sealed.

Equipment Parameters of TSA:

Apparatus: LightCycler 480 Real-Time PCR System (Roche Applied Science)

Scan rate: 0.02° C./sec

Scan range: 37° C.-96° C.

Integration time: 1.0 sec

Excitation wave length 465 nm

Emission wave length 580 nm

The obtained fluorescence signal was normalized into a range of 0 and 1. The denaturing temperature (Td) was defined as the temperature where the normalized value is closest to 0.5. The temperature where the maximum signal intensity (normalized value is 1) was defined as Td2 and it used for an index of thermostability of *Myceliophthora sepedonium* GH37 trehalase variants.

Trehalase Assay

Ten microliters of sample was mixed with 190 µl of substrate solution (1% trehalose in 50 mM sodium acetate, pH 4.3) and incubate at 32° C. for 1 hour. 10 µl of the solution was then taken out and 200 µl of glucose CII test WAKO (Wako Pure Chemical Industries, Osaka, Japan) was added. A505 was measured after 15 min-incubation at room temperature.

SF Cultivation for Protease Cocktail Preparation

*Aspergillus niger* strains used to prepare protease cocktail is derivatives of NN059095, which was isolated by Novozymes and genetically modified to disrupt expression of amyloglycosidase activities from *Aspergillus niger* NN049184 isolated from soil.

Spores of *Aspergillus niger* strains were inoculated in 100 ml MLC media and cultivated at 30° C. for 2 days. 10 ml of MLC was inoculated to 100 ml of MU-1 medium and cultivated at 30° C. for 7 days. The supernatant was obtained by centrifugation.

MLC is composed of 40 g glucose, 50 g soybean powder, 4 g citric acid (pH 5) and water to 1 liter.

MU-1-glu is composed of 260 g glucose, 3 g $MgSO_4.7H_2O$, 5 g $KH_2PO_4$, 6 g $K_2SO_4$, 0.5 ml of trace metal solution and 2 g urea (pH 4.5) and water to 1 liter.

Trace metal solution is composed of 6.8 g $ZnCl_2.7H_2O$, 2.5 g $CuSO_4.5H_2O$, 0.24 g $NiCl_2.6H_2O$, 13.9 g $FeSO_4.7H_2O$, 13.5 g $MnSO_4.H_2O$ and 3 g citric acid and water to 1 liter.

Protease Stability Assay

Purified enzyme was diluted to 2 mg/ml with 50 mM sodium acetate buffer pH 4.0 and 100 µl of the sample was mixed with 100 µl of prepared protease cocktail. The solution was then incubated at −20° C., 4° C., 30° C. and 40° C. for 3 days and the residual activity was measured by trehalase assay.

The results of the performed tests are shown in table 2.

Results

TABLE 2

Ms-trehalase variants

| Variants | Td2 [° C.] | Protease stabilty* | | |
|---|---|---|---|---|
| | | 4° C. | 30° C. | 40° C. |
| M-trehalase (WT) | 65.5 | 90% | 42% | 15% |
| JTH001 | 65.5 | 100% | 58% | 17% |
| JTH061 | 66.2 | 100% | 82% | 38% |
| JTH062 | 66.9 | 100% | 80% | 34% |
| JTH063 | 65.8 | 100% | 68% | 26% |
| JTH064 | 66.3 | 100% | 74% | 30% |
| JTH065 | 67.6 | 100% | 80% | 37% |
| JTH066 | 67.4 | 100% | 86% | 35% |
| JTH067 | 67.4 | 97% | 76% | 31% |
| JTH076 | 65.7 | 100% | 68% | 24% |
| JTH078 | 66.0 | 100% | 58% | 18% |

*Residual activity after 3 days-incubation in an admixture with protease cocktail (−20° C. as 100%)

The invention claimed is:

1. A trehalase variant polypeptide having increased stability against protease degradation and/or increased thermo-stability compared to SEQ ID NO: 1, comprising a substitution at one or more positions corresponding to position 152, 182, 185, or 583 of SEQ ID NO: 1, wherein the variant has at least 80%, but less than 100% sequence identity to amino acids 1 to 674 of SEQ ID NO: 1 and wherein the variant has trehalase activity.

2. The variant of claim 1, which comprises one or more substitutions selected from the group consisting of P152G, P152E, P152A, F182V, F185R, or G583T.

3. The variant of claim 1 having an increase in stability against protease degradation compared to SEQ ID NO: 1, comprising a substitution or combination of substitutions selected from:
G583T;
P152G;
P152E;
P152A;
F182V;
F185R;
P152G+G583T;
F185R+G583T;
P152A+F182V+G583T; and
and wherein the variant has at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity and wherein the residual activity after 3 days incubation with *A. niger* protease mixture at 30° C., pH 4.0 is at least 50%, at least 60%, at least 70%, or at least 80%.

4. The variant of claim 1 having an increase in thermo-stability compared to SEQ ID NO: 1, comprising a substitution or combination of substitutions selected from:
P152G;
P152E;
P152A;
F182V;
F185R;
P152G+G583T;
F185R+G583T;
P152A+F182V+G583T; and
F182V+F185R+G583T;
and wherein the variant has at least 80%, at least 85%, at least 90%, at least 95%, at least 96%, at least 97%, at least 98%, or at least 99%, but less than 100% sequence identity to amino acids 1 to 674 of SEQ ID NO: 1 and wherein the variant has trehalase activity and wherein the thermal denaturing temperature measure by TSA assay is at least 65.7° C.

5. The variant of claim 4, wherein the thermal denaturing temperature is at least 65.8° C., at least 65.9° C., at least 66.0° C., at least 66.1° C., at least 66.2° C., at least 66.3° C., at least 66.4° C., at least 66.5° C., at least 66.6° C., at least 66.6° C., at least 66.8° C., at least 66.9° C., at least 67.0° C., at least 67.1° C., at least 67.2° C., at least 67.3° C., at least 67.4° C., at least 67.5° C.

6. A composition comprising a trehalase variant polypeptide having increased stability against protease degradation and/or increased thermo-stability compared to SEQ ID NO: 1, the trehalase variant polypeptide comprising a substitution at one or more positions corresponding to position 152, 182, 185, or 583 of SEQ ID NO: 1, wherein the variant has at least 80%, but less than 100% sequence identity to amino acids 1 to 674 of SEQ ID NO: 1 and wherein the variant has trehalase activity.

7. A whole broth formulation or cell culture composition comprising the polypeptide of claim 1.

8. The variant of claim 1, wherein the variant has at least 85%, but less than 100% sequence identity to amino acids 1 to 674 of SEQ ID NO: 1 and wherein the variant has trehalase activity.

9. The variant of claim 1, wherein the variant has at least 90%, but less than 100% sequence identity to amino acids 1 to 674 of SEQ ID NO: 1 and wherein the variant has trehalase activity.

10. The variant of claim 1, wherein the variant has at least 95%, but less than 100% sequence identity to amino acids 1 to 674 of SEQ ID NO: 1 and wherein the variant has trehalase activity.

11. The variant of claim 1, wherein the variant has at least 97%, but less than 100% sequence identity to amino acids 1 to 674 of SEQ ID NO: 1 and wherein the variant has trehalase activity.

12. The variant of claim 1, wherein the variant has at least 99%, but less than 100% sequence identity to amino acids 1 to 674 of SEQ ID NO: 1 and wherein the variant has trehalase activity.

13. The composition of claim 6, wherein the variant has at least 85%, but less than 100% sequence identity to amino acids 1 to 674 of SEQ ID NO: 1 and wherein the variant has trehalase activity.

14. The composition of claim 6, wherein the variant has at least 90%, but less than 100% sequence identity to amino acids 1 to 674 of SEQ ID NO: 1 and wherein the variant has trehalase activity.

15. The composition of claim 6, wherein the variant has at least 95%, but less than 100% sequence identity to amino acids 1 to 674 of SEQ ID NO: 1 and wherein the variant has trehalase activity.

16. The composition of claim 6, wherein the variant has at least 97%, but less than 100% sequence identity to amino acids 1 to 674 of SEQ ID NO: 1 and wherein the variant has trehalase activity.

17. The composition of claim 6, wherein the variant has at least 99%, but less than 100% sequence identity to amino acids 1 to 674 of SEQ ID NO: 1 and wherein the variant has trehalase activity.

* * * * *

SEQUENCE LISTING

<160> NUMBER OF SEQ ID NOS: 19

<210> SEQ ID NO 1
<211> LENGTH: 674
<212> TYPE: PRT
<213> ORGANISM: Myceliophthora sepedonium

<400> SEQUENCE: 1

```
Leu Tyr Ile Asn Gly Ser Val Thr Ala Pro Cys Asp Ser Pro Ile Tyr
1               5                   10                  15

Cys Gln Gly Glu Leu Leu Lys Ala Val Glu Leu Ala Arg Pro Phe Val
            20                  25                  30

Asp Ser Lys Thr Phe Val Asp Met Pro Thr Ile Lys Pro Val Asp Glu
        35                  40                  45

Val Leu Ala Ala Phe Ser Lys Leu Ser Leu Pro Leu Ser Asn Asn Ser
    50                  55                  60

Glu Leu Asn Ala Phe Leu Tyr Glu Asn Phe Ala Gln Ala Gly His Glu
65                  70                  75                  80

Leu Glu Glu Val Pro Asp Ser Glu Leu Glu Thr Asp Ala Lys Phe Leu
                85                  90                  95

Asp Lys Leu Glu Asp Arg Thr Ile Lys Glu Phe Val Gly Lys Val Ile
            100                 105                 110

Asp Ile Trp Pro Asp Leu Thr Arg Arg Tyr Ala Gly Pro Ser Asn Cys
        115                 120                 125

Thr Glu Cys Ala Asn Ser Phe Ile Pro Val Asn Arg Thr Phe Val Val
    130                 135                 140

Ala Gly Gly Arg Phe Arg Glu Pro Tyr Tyr Trp Asp Ser Tyr Trp Ile
145                 150                 155                 160

Val Glu Gly Leu Leu Arg Thr Gly Gly Ala Phe Thr His Ile Ser Lys
                165                 170                 175

Asn Ile Ile Glu Asn Phe Leu Asp Phe Val Asp Thr Ile Gly Phe Ile
            180                 185                 190

Pro Asn Gly Ala Arg Ile Tyr Tyr Leu Asn Arg Ser Gln Pro Pro Leu
        195                 200                 205

Leu Thr Leu Met Val Lys Ser Tyr Val Asp Tyr Thr Asn Asp Thr Ser
    210                 215                 220

Ile Leu Asp Arg Ala Leu Pro Leu Leu Ile Lys Glu His Glu Phe Phe
225                 230                 235                 240

Met Asn Asn Arg Thr Val Ser Ile Thr Gly Ser Asn Gly Lys Glu Tyr
                245                 250                 255

Thr Leu Asn Arg Tyr His Val Glu Asn Asn Gln Pro Arg Pro Glu Ser
            260                 265                 270

Phe Arg Glu Asp Tyr Ile Thr Ala Asn Asn Gly Ser Tyr Tyr Ala Ser
        275                 280                 285

Ser Gly Ile Ile Tyr Pro Val Lys Thr Pro Leu Asn Glu Thr Glu Lys
    290                 295                 300

Ala Ala Leu Tyr Ser Asn Leu Ala Thr Gly Ala Glu Ser Gly Trp Asp
305                 310                 315                 320

Tyr Thr Ser Arg Trp Leu Gly Val Pro Ser Asp Ala Ala Arg Asp Val
                325                 330                 335

Tyr Phe Pro Leu Arg Ser Leu Asn Val Arg Asp Ile Val Pro Val Asp
            340                 345                 350

Leu Asn Ser Ile Leu Tyr Gln Asn Glu Val Ile Ile Ala Glu Tyr Leu
        355                 360                 365
```

| | | | | | | | | | | | |
|---|---|---|---|---|---|---|---|---|---|---|---|
|Glu|Lys|Ala|Gly|Asn|Ser|Ser|Ala|Ala|Lys|Arg|Phe|Ala|Thr|Ala|Ala|
|370| | | | |375| | | | |380| | | | | |

Glu Gln Arg Ser Glu Ala Met Tyr Ser Leu Met Trp Asn Ala Thr His
385                     390                     395                     400

Trp Ser Tyr Phe Asp Tyr Asn Leu Thr Asp Asn Thr Gln His Ile Phe
                405                     410                     415

Val Pro Ala Asp Glu Asp Thr Ala Pro Gln Asp Arg Ile Glu Ala Pro
                420                     425                     430

Pro Gly Gln Gln Val Phe Phe His Ile Ala Gln Leu Tyr Pro Phe Trp
                435                     440                     445

Thr Gly Ala Ala Pro Ala Ser Leu Lys Ala Asn Pro Leu Ala Val Gln
450                     455                     460

Gln Ala Tyr Ala Arg Val Ala Arg Met Leu Asp Ile Lys Lys Gly Ala
465                     470                     475                     480

Ile Pro Ala Thr Asn Tyr Arg Thr Gly Gln Gln Trp Asp Gln Pro Asn
                485                     490                     495

Val Trp Pro Pro Leu Gln His Ile Leu Met Lys Gly Leu Leu Asn Thr
                500                     505                     510

Pro Ala Thr Phe Gly Lys Ser Asp Pro Ala Tyr Gln Ser Val Gln Asn
                515                     520                     525

Leu Ala Leu Arg Leu Ala Gln Arg Tyr Leu Asp Ser Thr Phe Cys Thr
530                     535                     540

Trp Tyr Ala Thr Gly Gly Ser Thr Ser Asp Phe Pro Gln Leu Glu Gly
545                     550                     555                     560

Val Thr Pro Gly Ala Thr Gly Val Met Phe Glu Lys Tyr Ala Asp Asn
                565                     570                     575

Ala Thr Asn Val Ala Gly Gly Gly Glu Tyr Glu Val Val Glu Gly
                580                     585                     590

Phe Gly Trp Thr Asn Gly Val Leu Ile Trp Ala Ala Asp Val Phe Gly
                595                     600                     605

Asn Lys Leu Lys Arg Pro Asp Cys Gly Asn Ile Thr Ala Ala His Thr
610                     615                     620

His Ser Ser Ala Lys Arg Gly Leu Glu Glu Asn Lys Leu Pro Arg Arg
625                     630                     635                     640

Ala Val Glu Leu Asp Pro Trp Asp Ala Ala Trp Thr Lys Met Phe Gly
                645                     650                     655

Arg Ser Lys Leu Arg Arg Glu Ala Glu Asp Val Arg Lys Arg Trp
                660                     665                     670

Met Ser

<210> SEQ ID NO 2
<211> LENGTH: 2229
<212> TYPE: DNA
<213> ORGANISM: Myceliophthora sepedonium

<400> SEQUENCE: 2

```
atggcgctac gacacatcgc ggcggcggcg atcgccggtc ttgcctcaag gactgcagcg     60
ctgtacatca atggctcagt cacagcgccg tgcgactcgc ccatttactg ccaaggcgag    120
cttctaaaag cggttgaact ggcgcgtcct tcgttgaca gcaagacatt tgtggacatg     180
taagtcatga tcggccagcc aggtgggaat gcagccggcg gcagattcg tggtgacaca     240 ctgactgact ggattcccg cccaggccca cgatcaagcc agtggatgaa gtgcttgcag     300
cattcagcaa gcttagccta ccactttcca ataactcaga gctcaacgcc ttcttgtatg    360
```

```
agaacttcgc ccaggctggc cacgagctcg aagaagtgcc cgacagtgag ctagagacgg      420
acgcaaagtt cctcgacaag ctcgaggatc gcaccatcaa ggagttcgtc ggcaaggtga      480
tcgacatctg gcccgacttg accaggcgct atgccggccc cagcaactgc accgagtgcg      540
ccaacagctt cattcccgtg aaccgcacgt tcgtcgtggc tggcggtcgc ttccgagagc      600
cctactattg ggattcgtac tggatcgtcg aaggtctcct gcgcactggc ggtgccttca      660
cccatatctc caagaacatc attgagaact tcctggactt tgtcgacacg attggcttca      720
ttcccaatgg cgccaggatc tactacctga acaggtcaca gcccctctc ctgacattga      780 tggtgaagag ctacgtcgac tacaccaacg acacgagcat cctggacagg gccttgccgc      840
tgctgatcaa ggagcacgag ttcttcatga ataaccggac ggtgtccatc acgggatcga      900
acggcaagga gtacactctg aacaggtaag cgaggtggac aggcaggcct cggcgaccat      960
gcgcttattg ttgtatctgg caggtatcac gttgaaaaca accaaccacg cccagagtcg     1020
ttccgggagg attacattac cgctaacaac ggctccctact acgcgtcttc gggcataata     1080
tatcccgtta agacgcccct caacgagacg gaaaaggccg cgctctactc gaacctagca     1140
accggcgccg agtccggctg ggactacacc tcccgatggc ttggggtccc cagcgacgct     1200
gcgagggacg tctatttccc gctccgctcg cttaatgtcc gcgacatagt ccccgtcgat     1260
ctcaactcca tcctctacca gaacgaggtg atcattgccg agtacctcga aaggccggt      1320 aactcctccg cggccaagcg cttcgccact gctgccgaac agcgcagcga ggccatgtac     1380
tccctcatgt ggaacgccac gcactggtct tactttgact acaatctgac cgataacacg     1440
caacacatct tcgtcccagc cgacgaggac accgccccc aggaccggat cgaggccccc      1500
cccggtcaac aagtcttctt ccacattgcg cagctctatc cattctggac gggcgcggcc     1560
cccgccagcc ttaaggctaa ccccctcgcg gtgcagcaag cctacgcccg tgtggcgcgc     1620
atgctcgata tcaagaaggg cgccatcccc gccaccaact accgcaccgg ccaacaatgg     1680
gaccagccca acgtctggcc gccgctgcaa catatcctga tgaagggcct gcttaacacc     1740
ccggcaacct ttggcaagtc cgaccctgcg taccagagcg tgcaaaacct cgccctgcgt     1800
ctcgcccagc gctacctcga ttccacctt tgtacctggt acgccacggg cggttcaacc      1860
agcgacttcc cgcagctgga gggtgttacc ccggcgcta cgggcgtcat gtttgagaag     1920
tacgccgaca tgctaccaa cgttgccggc ggcggcggcg aatacgaggt cgtcgagggt      1980
ttcgggtgga ccaatggcgt actgatctgg gcggccgacg tctttggtaa caagctcaag     2040
cgcccggact gcggcaacat cacggccgca catacccact ctagtgccaa gagaggtctg     2100
gaagagaata gctgccgag agggcggtg gagctcgacc cgtgggatgc cgcgtggacc      2160
aagatgtttg gcggagtaa gctccggaga agagaggcag aagatgtgcg gaagcggtgg     2220
atgagctaa                                                             2229
```

<210> SEQ ID NO 3
<211> LENGTH: 2085
<212> TYPE: DNA
<213> ORGANISM: Myceliophthora sepedonium

<400> SEQUENCE: 3

```
atggcgctac gacacatcgc ggcggcggcg atcgccggtc ttgcctcaag gactgcagcg       60
ctgtacatca atggctcagt cacagcgccg tgcgactcgc ccatttactg ccaaggcgag      120
cttctaaaag cggttgaact ggcgcgtcct ttcgttgaca gcaagacatt tgtggacatg      180
cccacgatca agccagtgga tgaagtgctt gcagcattca gcaagcttag cctaccactt      240
```

-continued

```
tccaataact cagagctcaa cgccttcttg tatgagaact tcgcccaggc tggccacgag    300
ctcgaagaag tgcccgacag tgagctagag acggacgcaa agttcctcga caagctcgag    360
gatcgcacca tcaaggagtt cgtcggcaag gtgatcgaca tctggcccga cttgaccagg    420
cgctatgccg gccccagcaa ctgcaccgag tgcgccaaca gcttcattcc cgtgaaccgc    480
acgttcgtcg tggctggcgg tcgcttccga gagccctact attgggattc gtactggatc    540
gtcgaaggtc tcctgcgcac tggcggtgcc ttcacccata tctccaagaa catcattgag    600
aacttcctgg actttgtcga cacgattggc ttcattccca atggcgccag gatctactac    660
ctgaacaggt cacagccccc tctcctgaca ttgatggtga agagctacgt cgactacacc    720
aacgacacga gcatcctgga cagggccttg ccgctgctga tcaaggagca cgagttcttc    780
atgaataacc ggacggtgtc catcacggga tcgaacggca aggagtacac tctgaacagg    840
tatcacgttg aaaacaacca accacgccca gagtcgttcc gggaggatta cattaccgct    900
aacaacggct cctactacgc gtcttcgggc ataatatatc ccgttaagac gcccctcaac    960
gagacggaaa aggccgcgct ctactcgaac ctagcaaccg cgccgagtc cggctgggac   1020
tacacctccc gatggcttgg ggtccccagc gacgctgcga gggacgtcta tttcccgctc   1080
cgctcgctta atgtccgcga catagtcccc gtcgatctca actccatcct ctaccagaac   1140
gaggtgatca ttgccgagta cctcgagaag gccggtaact cctccgcggc caagcgcttc   1200
gccactgctg ccgaacagcg cagcgaggcc atgtactccc tcatgtggaa cgccacgcac   1260
tggtcttact ttgactacaa tctgaccgat aacacgcaac acatcttcgt cccagccgac   1320
gaggacaccg ccccccagga ccggatcgag gcccccccg gtcaacaagt cttcttccac   1380
attgcgcagc tctatccatt ctggacgggc gcggcccccg ccagccttaa ggctaacccc   1440
ctcgcggtgc agcaagccta cgcccgtgtg gcgcgcatgc tcgatatcaa gagggcgcc    1500
atccccgcca ccaactaccg caccggccaa caatgggacc agcccaacgt ctggccgccg   1560
ctgcaacata tcctgatgaa gggcctgctt aacaccccgg caacctttgg caagtccgac   1620
cctgcgtacc agagcgtgca aaacctcgcc ctgcgtctcg cccagcgcta cctcgattcc   1680
acctttgta cctggtacgc cacgggcggt tcaaccagcg acttcccgca gctggagggt   1740
gttaccccgg gcgctacggg cgtcatgttt gagaagtacg ccgacaatgc taccaacgtt   1800
gccggcggcg gcggcgaata cgaggtcgtc gagggtttcg ggtggaccaa tggcgtactg   1860
atctgggcgc ccgacgtctt tggtaacaag ctcaagcgcc cggactgcgg caacatcacg   1920
gccgcacata cccactctag tgccaagaga ggtctggaag agaataagct gccgaggagg   1980
gcggtggagc tcgaccccgtg gatgccgcg tggaccaaga tgtttgggcg gagtaagctc   2040
cggagaagag aggcagaaga tgtgcggaag cggtggatga gctaa               2085
```

<210> SEQ ID NO 4
<211> LENGTH: 598
<212> TYPE: PRT
<213> ORGANISM: Talaromyces emersonii

<400> SEQUENCE: 4

Arg Ala Pro Val Ala Ala Arg Ala Thr Gly Ser Leu Asp Ser Phe Leu
1               5                   10                  15

Ala Thr Glu Thr Pro Ile Ala Leu Gln Gly Val Leu Asn Asn Ile Gly
            20                  25                  30

Pro Asn Gly Ala Asp Val Ala Gly Ala Ser Ala Gly Ile Val Val Ala
        35                  40                  45

```
Ser Pro Ser Arg Ser Asp Pro Asn Tyr Phe Tyr Ser Trp Thr Arg Asp
    50              55                  60

Ala Ala Leu Thr Ala Lys Tyr Leu Val Asp Ala Phe Ile Ala Gly Asn
 65              70                  75                      80

Lys Asp Leu Glu Gln Thr Ile Gln Gln Tyr Ile Ser Ala Gln Ala Lys
                 85                  90                  95

Val Gln Thr Ile Ser Asn Pro Ser Gly Asp Leu Ser Thr Gly Gly Leu
                100             105             110

Gly Glu Pro Lys Phe Asn Val Asn Glu Thr Ala Phe Thr Gly Pro Trp
            115             120             125

Gly Arg Pro Gln Arg Asp Gly Pro Ala Leu Arg Ala Thr Ala Leu Ile
130             135             140

Ala Tyr Ala Asn Tyr Leu Ile Asp Asn Gly Glu Ala Ser Thr Ala Asp
145             150             155             160

Glu Ile Ile Trp Pro Ile Val Gln Asn Asp Leu Ser Tyr Ile Thr Gln
                165             170             175

Tyr Trp Asn Ser Ser Thr Phe Asp Leu Trp Glu Glu Val Glu Gly Ser
            180             185             190

Ser Phe Phe Thr Thr Ala Val Gln His Arg Ala Leu Val Glu Gly Asn
        195             200             205

Ala Leu Ala Thr Arg Leu Asn His Thr Cys Ser Asn Cys Val Ser Gln
210             215             220

Ala Pro Gln Val Leu Cys Phe Leu Gln Ser Tyr Trp Thr Gly Ser Tyr
225             230             235             240

Val Leu Ala Asn Phe Gly Gly Ser Gly Arg Ser Gly Lys Asp Val Asn
                245             250             255

Ser Ile Leu Gly Ser Ile His Thr Phe Asp Pro Ala Gly Gly Cys Asp
            260             265             270

Asp Ser Thr Phe Gln Pro Cys Ser Ala Arg Ala Leu Ala Asn His Lys
        275             280             285

Val Val Thr Asp Ser Phe Arg Ser Ile Tyr Ala Ile Asn Ser Gly Ile
290             295             300

Ala Glu Gly Ser Ala Val Ala Val Gly Arg Tyr Pro Glu Asp Val Tyr
305             310             315             320

Gln Gly Gly Asn Pro Trp Tyr Leu Ala Thr Ala Ala Ala Glu Gln
            325             330             335

Leu Tyr Asp Ala Ile Tyr Gln Trp Lys Lys Ile Gly Ser Ile Ser Ile
            340             345             350

Thr Asp Val Ser Leu Pro Phe Phe Gln Asp Ile Tyr Pro Ser Ala Ala
            355             360             365

Val Gly Thr Tyr Asn Ser Gly Ser Thr Thr Phe Asn Asp Ile Ile Ser
    370             375             380

Ala Val Gln Thr Tyr Gly Asp Gly Tyr Leu Ser Ile Val Glu Lys Tyr
385             390             395             400

Thr Pro Ser Asp Gly Ser Leu Thr Glu Gln Phe Ser Arg Thr Asp Gly
                405             410             415

Thr Pro Leu Ser Ala Ser Ala Leu Thr Trp Ser Tyr Ala Ser Leu Leu
            420             425             430

Thr Ala Ser Ala Arg Arg Gln Ser Val Val Pro Ala Ser Trp Gly Glu
            435             440             445

Ser Ser Ala Ser Ser Val Pro Ala Val Cys Ser Ala Thr Ser Ala Thr
450             455             460
```

Gly Pro Tyr Ser Thr Ala Thr Asn Thr Val Trp Pro Ser Ser Gly Ser
465                 470                 475                 480

Gly Ser Ser Thr Thr Thr Ser Ser Ala Pro Cys Thr Thr Pro Thr Ser
            485                 490                 495

Val Ala Val Thr Phe Asp Glu Ile Val Ser Thr Ser Tyr Gly Glu Thr
            500                 505                 510

Ile Tyr Leu Ala Gly Ser Ile Pro Glu Leu Gly Asn Trp Ser Thr Ala
            515                 520                 525

Ser Ala Ile Pro Leu Arg Ala Asp Ala Tyr Thr Asn Ser Asn Pro Leu
            530                 535                 540

Trp Tyr Val Thr Val Asn Leu Pro Pro Gly Thr Ser Phe Glu Tyr Lys
545                 550                 555                 560

Phe Phe Lys Asn Gln Thr Asp Gly Thr Ile Val Trp Glu Asp Asp Pro
            565                 570                 575

Asn Arg Ser Tyr Thr Val Pro Ala Tyr Cys Gly Gln Thr Thr Ala Ile
            580                 585                 590

Leu Asp Asp Ser Trp Gln
            595

<210> SEQ ID NO 5
<211> LENGTH: 556
<212> TYPE: PRT
<213> ORGANISM: Gloeophyllum sepiarium

<400> SEQUENCE: 5

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Ala Ser Pro Ser Thr Ser Asp Pro Asp Tyr
            35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ser Thr Ala Leu Ile Thr Tyr Gly Asn Trp Leu
    130                 135                 140

Leu Ser Asn Gly Asn Thr Ser Tyr Val Thr Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Phe Phe Thr Thr Ala
            180                 185                 190

Val Gln His Arg Ala Leu Arg Glu Gly Ala Ala Phe Ala Thr Ala Ile
            195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
        245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Val Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
        355                 360                 365

Tyr Ser Ser Ser Ser Thr Tyr Ser Thr Leu Thr Ser Ala Ile Lys
    370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
        435                 440                 445

Thr Val Pro Ser Ser Cys Ser Gly Asn Ser Gly Gly Pro Thr Val Ala
    450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
    530                 535                 540

Ala Ser Gly Ser Thr Thr Glu Asn Asp Thr Trp Arg
545                 550                 555

<210> SEQ ID NO 6
<211> LENGTH: 559
<212> TYPE: PRT
<213> ORGANISM: Gloephyllum trabeum

<400> SEQUENCE: 6

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

```
Asp Gln Tyr Thr Thr Gly Ile Asp Ser Thr Ser Leu Arg Ser Leu
 65                  70                  75                  80

Ile Asp Ser Phe Val Ile Ala Glu Ala Asn Ile Gln Gln Val Ser Asn
                 85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
                180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Ile Ala Ser Asn
                290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
                340                 345                 350

Ser Leu Pro Phe Phe Gln Gln Phe Ser Ser Ser Val Thr Ala Gly Thr
                355                 360                 365

Tyr Ala Ser Ser Ser Thr Thr Tyr Thr Thr Leu Thr Ser Ala Ile Lys
            370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
        435                 440                 445

Thr Val Pro Thr Ser Cys Ser Ser Asn Ser Gly Gly Gly Gly Ser
    450                 455                 460

Thr Val Ala Val Thr Phe Asn Val Asn Ala Gln Thr Val Trp Gly Glu
465                 470                 475                 480
```

```
Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
            515                 520                 525

Lys Asn Asn Gly Ala Val Thr Trp Glu Ser Asp Pro Asn Asn Ser Ile
        530                 535                 540

Thr Thr Pro Ala Ser Gly Ser Val Thr Glu Asn Asp Thr Trp Arg
545                 550                 555

<210> SEQ ID NO 7
<211> LENGTH: 583
<212> TYPE: PRT
<213> ORGANISM: Rhizomucor pusillus

<400> SEQUENCE: 7

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
290                 295                 300
```

```
Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
                340                 345                 350

Met Lys Ser Asn Lys Ala Val Tyr Met Asp Ile Tyr Val Gly Asp Asn
                355                 360                 365

Ala Tyr Ala Phe Lys His Gly Asp Ala Leu Val Val Leu Asn Asn Tyr
            370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
                420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
                515                 520                 525

Leu Trp Tyr Val Thr Val Thr Leu Pro Ala Gly Glu Ser Phe Glu Tyr
                530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
                580
```

<210> SEQ ID NO 8
<211> LENGTH: 515
<212> TYPE: PRT
<213> ORGANISM: Bacillus stearothermophilus

<400> SEQUENCE: 8

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65              70                  75                  80

Lys Ala Gln Tyr Leu Gln Ala Ile Gln Ala Ala His Ala Ala Gly Met
                85                  90                  95
```

-continued

Gln Val Tyr Ala Asp Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510
Ala Trp Pro
        515

<210> SEQ ID NO 9
<211> LENGTH: 413
<212> TYPE: PRT
<213> ORGANISM: Pyrococcus furiosus

<400> SEQUENCE: 9

Ala Glu Leu Glu Gly Leu Asp Glu Ser Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

```
Tyr Asp Pro Asn Gly Asn Gln Val Asp Tyr Ser Tyr Thr Ala Tyr Tyr
            355                 360                 365

Asp Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 10
<211> LENGTH: 595
<212> TYPE: PRT
<213> ORGANISM: Penicillium oxalicum

<400> SEQUENCE: 10

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
290                 295                 300

Lys Ile Asn Ala Gly Leu Ala Glu Gly Ser Ala Ala Asn Val Gly Arg
305                 310                 315                 320
```

Tyr Pro Glu Asp Val Tyr Gln Gly Gly Asn Pro Trp Tyr Leu Ala Thr
            325                 330                 335

Leu Gly Ala Ser Glu Leu Leu Tyr Asp Ala Leu Tyr Gln Trp Asp Arg
        340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
            405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
        450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
            485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
        530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
            565                 570                 575

Phe Val Ala Pro Thr Gly Cys Pro Val Gln Pro His Ser Asn Asp Val
            580                 585                 590

Trp Gln Phe
        595

<210> SEQ ID NO 11
<211> LENGTH: 556
<212> TYPE: PRT
<213> ORGANISM: Trametes cingulata

<400> SEQUENCE: 11

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
            85                  90                  95

```
Pro Ser Gly Thr Val Ser Gly Gly Leu Gly Glu Pro Lys Phe Asn
                100             105             110

Ile Asp Glu Thr Ala Phe Thr Asp Ala Trp Gly Arg Pro Gln Arg Asp
    115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
                180                 185                 190

Val Gln His Arg Ala Leu Arg Glu Gly Ala Thr Phe Ala Asn Arg Ile
            195                 200                 205

Gly Gln Thr Ser Val Val Ser Gly Tyr Thr Thr Gln Ala Asn Asn Leu
        210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
                260                 265                 270

Phe Gln Pro Cys Ser Asp Lys Ala Leu Ser Asn Leu Lys Val Tyr Val
            275                 280                 285

Asp Ala Phe Arg Ser Ile Tyr Ser Ile Asn Ser Gly Ile Ala Ser Asn
        290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
                340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
        370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Leu Thr Ser Phe
                420                 425                 430

Ala Ala Arg Ser Gly Lys Thr Tyr Ala Ser Trp Gly Ala Ala Gly Leu
            435                 440                 445

Thr Val Pro Thr Thr Cys Ser Gly Ser Gly Ala Gly Thr Val Ala
        450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510
```

```
Leu Pro Ala Ser Thr Thr Ile Glu Tyr Lys Tyr Ile Arg Lys Phe Asn
            515                 520                 525

Gly Ala Val Thr Trp Glu Ser Asp Pro Asn Asn Ser Ile Thr Thr Pro
            530                 535                 540

Ala Ser Gly Thr Phe Thr Gln Asn Asp Thr Trp Arg
545                 550                 555

<210> SEQ ID NO 12
<211> LENGTH: 555
<212> TYPE: PRT
<213> ORGANISM: Pycnoporus sanguineus

<400> SEQUENCE: 12

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
            35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
            115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
            180                 185                 190

Val Gln His Arg Ala Leu Arg Glu Gly Ala Thr Phe Ala Ser Arg Ile
            195                 200                 205

Gly Gln Ser Ser Val Val Ser Gly Tyr Thr Thr Gln Ala Asp Asn Leu
    210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
            275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335
```

-continued

```
Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
    370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Leu Thr Ala Phe
            420                 425                 430

Ala Ala Arg Glu Gly Lys Thr Tyr Gly Ser Trp Gly Ala Ala Gly Leu
        435                 440                 445

Thr Val Pro Ala Ser Cys Ser Gly Gly Gly Ala Thr Val Ala Val
    450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555

<210> SEQ ID NO 13
<211> LENGTH: 177
<212> TYPE: PRT
<213> ORGANISM: Thermoascus aurantiacus

<400> SEQUENCE: 13

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160
```

```
Met Asn Ala Asp Thr Tyr Ala Leu Tyr Ala Asn Ala Ile Tyr Leu Gly
                165                 170                 175
Cys

<210> SEQ ID NO 14
<211> LENGTH: 844
<212> TYPE: PRT
<213> ORGANISM: Aspergillus fumigatus

<400> SEQUENCE: 14

Gln Glu Leu Ala Phe Ser Pro Pro Phe Tyr Pro Ser Pro Trp Ala Asp
1               5                   10                  15

Gly Gln Gly Glu Trp Ala Asp Ala His Arg Arg Ala Val Glu Ile Val
            20                  25                  30

Ser Gln Met Thr Leu Ala Glu Lys Val Asn Leu Thr Thr Gly Thr Gly
        35                  40                  45

Trp Glu Met Asp Arg Cys Val Gly Gln Thr Gly Ser Val Pro Arg Leu
    50                  55                  60

Gly Ile Asn Trp Gly Leu Cys Gly Gln Asp Ser Pro Leu Gly Ile Arg
65                  70                  75                  80

Phe Ser Asp Leu Asn Ser Ala Phe Pro Ala Gly Thr Asn Val Ala Ala
                85                  90                  95

Thr Trp Asp Lys Thr Leu Ala Tyr Leu Arg Gly Lys Ala Met Gly Glu
            100                 105                 110

Glu Phe Asn Asp Lys Gly Val Asp Ile Leu Leu Gly Pro Ala Ala Gly
        115                 120                 125

Pro Leu Gly Lys Tyr Pro Asp Gly Gly Arg Ile Trp Glu Gly Phe Ser
    130                 135                 140

Pro Asp Pro Val Leu Thr Gly Val Leu Phe Ala Glu Thr Ile Lys Gly
145                 150                 155                 160

Ile Gln Asp Ala Gly Val Ile Ala Thr Ala Lys His Tyr Ile Leu Asn
                165                 170                 175

Glu Gln Glu His Phe Arg Gln Val Gly Glu Ala Gln Gly Tyr Gly Tyr
            180                 185                 190

Asn Ile Thr Glu Thr Ile Ser Ser Asn Val Asp Asp Lys Thr Met His
        195                 200                 205

Glu Leu Tyr Leu Trp Pro Phe Ala Asp Ala Val Arg Ala Gly Val Gly
    210                 215                 220

Ala Val Met Cys Ser Tyr Asn Gln Ile Asn Asn Ser Tyr Gly Cys Gln
225                 230                 235                 240

Asn Ser Gln Thr Leu Asn Lys Leu Leu Lys Ala Glu Leu Gly Phe Gln
                245                 250                 255

Gly Phe Val Met Ser Asp Trp Ser Ala His His Ser Gly Val Gly Ala
            260                 265                 270

Ala Leu Ala Gly Leu Asp Met Ser Met Pro Gly Asp Ile Ser Phe Asp
        275                 280                 285

Asp Gly Leu Ser Phe Trp Gly Thr Asn Leu Thr Val Ser Val Leu Asn
    290                 295                 300

Gly Thr Val Pro Ala Trp Arg Val Asp Asp Met Ala Val Arg Ile Met
305                 310                 315                 320

Thr Ala Tyr Tyr Lys Val Gly Arg Asp Arg Leu Arg Ile Pro Pro Asn
                325                 330                 335

Phe Ser Ser Trp Thr Arg Asp Glu Tyr Gly Trp Glu His Ser Ala Val
            340                 345                 350
```

```
Ser Glu Gly Ala Trp Thr Lys Val Asn Asp Phe Val Asn Val Gln Arg
            355                 360                 365

Ser His Ser Gln Ile Ile Arg Glu Ile Gly Ala Ala Ser Thr Val Leu
        370                 375                 380

Leu Lys Asn Thr Gly Ala Leu Pro Leu Thr Gly Lys Glu Val Lys Val
385                 390                 395                 400

Gly Val Leu Gly Glu Asp Ala Gly Ser Asn Pro Trp Gly Ala Asn Gly
                405                 410                 415

Cys Pro Asp Arg Gly Cys Asp Asn Gly Thr Leu Ala Met Ala Trp Gly
            420                 425                 430

Ser Gly Thr Ala Asn Phe Pro Tyr Leu Val Thr Pro Glu Gln Ala Ile
        435                 440                 445

Gln Arg Glu Val Ile Ser Asn Gly Asn Val Phe Ala Val Thr Asp
    450                 455                 460

Asn Gly Ala Leu Ser Gln Met Ala Asp Val Ala Ser Gln Ser Ser Val
465                 470                 475                 480

Ser Leu Val Phe Val Asn Ala Asp Ser Gly Glu Gly Phe Ile Ser Val
                485                 490                 495

Asp Gly Asn Glu Gly Asp Arg Lys Asn Leu Thr Leu Trp Lys Asn Gly
            500                 505                 510

Glu Ala Val Ile Asp Thr Val Val Ser His Cys Asn Asn Thr Ile Val
        515                 520                 525

Val Ile His Ser Val Gly Pro Val Leu Ile Asp Arg Trp Tyr Asp Asn
    530                 535                 540

Pro Asn Val Thr Ala Ile Ile Trp Ala Gly Leu Pro Gly Gln Glu Ser
545                 550                 555                 560

Gly Asn Ser Leu Val Asp Val Leu Tyr Gly Arg Val Asn Pro Ser Ala
                565                 570                 575

Lys Thr Pro Phe Thr Trp Gly Lys Thr Arg Glu Ser Tyr Gly Ala Pro
            580                 585                 590

Leu Leu Thr Glu Pro Asn Asn Gly Asn Gly Ala Pro Gln Asp Asp Phe
        595                 600                 605

Asn Glu Gly Val Phe Ile Asp Tyr Arg His Phe Asp Lys Arg Asn Glu
    610                 615                 620

Thr Pro Ile Tyr Glu Phe Gly His Gly Leu Ser Tyr Thr Thr Phe Gly
625                 630                 635                 640

Tyr Ser His Leu Arg Val Gln Ala Leu Asn Ser Ser Ser Ala Tyr
                645                 650                 655

Val Pro Thr Ser Gly Glu Thr Lys Pro Ala Pro Thr Tyr Gly Glu Ile
            660                 665                 670

Gly Ser Ala Ala Asp Tyr Leu Tyr Pro Glu Gly Leu Lys Arg Ile Thr
        675                 680                 685

Lys Phe Ile Tyr Pro Trp Leu Asn Ser Thr Asp Leu Glu Asp Ser Ser
    690                 695                 700

Asp Asp Pro Asn Tyr Gly Trp Glu Asp Ser Glu Tyr Ile Pro Glu Gly
705                 710                 715                 720

Ala Arg Asp Gly Ser Pro Gln Pro Leu Leu Lys Ala Gly Gly Ala Pro
                725                 730                 735

Gly Gly Asn Pro Thr Leu Tyr Gln Asp Leu Val Arg Val Ser Ala Thr
            740                 745                 750

Ile Thr Asn Thr Gly Asn Val Ala Gly Tyr Glu Val Pro Gln Leu Tyr
        755                 760                 765
```

```
Val Ser Leu Gly Gly Pro Asn Glu Pro Arg Val Val Leu Arg Lys Phe
    770                 775                 780

Asp Arg Ile Phe Leu Ala Pro Gly Glu Gln Lys Val Trp Thr Thr Thr
785                 790                 795                 800

Leu Asn Arg Arg Asp Leu Ala Asn Trp Asp Val Glu Ala Gln Asp Trp
                805                 810                 815

Val Ile Thr Lys Tyr Pro Lys Lys Val His Val Gly Ser Ser Ser Arg
                820                 825                 830

Lys Leu Pro Leu Arg Ala Pro Leu Pro Arg Val Tyr
                835                 840

<210> SEQ ID NO 15
<211> LENGTH: 227
<212> TYPE: PRT
<213> ORGANISM: Thermoascus aurantiacus

<400> SEQUENCE: 15

Phe Val Gln Asn Ile Val Ile Asp Gly Lys Lys Tyr Tyr Gly Gly Tyr
1               5                   10                  15

Leu Val Asn Gln Tyr Pro Tyr Met Ser Asn Pro Glu Val Ile Ala
            20                  25                  30

Trp Ser Thr Thr Ala Thr Asp Leu Gly Phe Val Asp Gly Thr Gly Tyr
        35                  40                  45

Gln Thr Pro Asp Ile Ile Cys His Arg Gly Ala Lys Pro Gly Ala Leu
    50                  55                  60

Thr Ala Pro Val Ser Pro Gly Gly Thr Val Glu Leu Gln Trp Thr Pro
65                  70                  75                  80

Trp Pro Asp Ser His His Gly Pro Val Ile Asn Tyr Leu Ala Pro Cys
                85                  90                  95

Asn Gly Asp Cys Ser Thr Val Asp Lys Thr Gln Leu Glu Phe Phe Lys
            100                 105                 110

Ile Ala Glu Ser Gly Leu Ile Asn Asp Asp Asn Pro Pro Gly Ile Trp
        115                 120                 125

Ala Ser Asp Asn Leu Ile Ala Ala Asn Asn Ser Trp Thr Val Thr Ile
    130                 135                 140

Pro Thr Thr Ile Ala Pro Gly Asn Tyr Val Leu Arg His Glu Ile Ile
145                 150                 155                 160

Ala Leu His Ser Ala Gln Asn Gln Asp Gly Ala Gln Asn Tyr Pro Gln
                165                 170                 175

Cys Ile Asn Leu Gln Val Thr Gly Gly Gly Ser Asp Asn Pro Ala Gly
            180                 185                 190

Thr Leu Gly Thr Ala Leu Tyr His Asp Thr Asp Pro Gly Ile Leu Ile
        195                 200                 205

Asn Ile Tyr Gln Lys Leu Ser Ser Tyr Ile Ile Pro Gly Pro Pro Leu
    210                 215                 220

Tyr Thr Gly
225

<210> SEQ ID NO 16
<211> LENGTH: 228
<212> TYPE: PRT
<213> ORGANISM: Penicillium emersonii
```

```
<400> SEQUENCE: 16

His Gly Phe Val Gln Gly Ile Val Ile Gly Asp Gln Phe Tyr Ser Gly
1               5                   10                  15

Tyr Ile Val Asn Ser Phe Pro Tyr Glu Ser Asn Pro Pro Val Ile
            20                  25                  30

Gly Trp Ala Thr Thr Ala Thr Asp Leu Gly Phe Val Asp Gly Thr Gly
            35                  40                  45

Tyr Gln Gly Pro Asp Ile Ile Cys His Arg Asn Ala Thr Pro Ala Pro
 50                  55                  60

Leu Thr Ala Pro Val Ala Ala Gly Gly Thr Val Glu Leu Gln Trp Thr
 65                  70                  75                  80

Pro Trp Pro Asp Ser His His Gly Pro Val Ile Thr Tyr Leu Ala Pro
                 85                  90                  95

Cys Asn Gly Asn Cys Ser Thr Val Asp Lys Thr Thr Leu Glu Phe Phe
                100                 105                 110

Lys Ile Asp Gln Gln Gly Leu Ile Asp Asp Thr Ser Pro Pro Gly Thr
                115                 120                 125

Trp Ala Ser Asp Asn Leu Ile Ala Asn Asn Ser Trp Thr Val Thr
    130                 135                 140

Ile Pro Asn Ser Val Ala Pro Gly Asn Tyr Val Leu Arg His Glu Ile
145                 150                 155                 160

Ile Ala Leu His Ser Ala Asn Asn Lys Asp Gly Ala Gln Asn Tyr Pro
                165                 170                 175

Gln Cys Ile Asn Ile Glu Val Thr Gly Gly Gly Ser Asp Ala Pro Glu
                180                 185                 190

Gly Thr Leu Gly Glu Asp Leu Tyr His Asp Thr Asp Pro Gly Ile Leu
                195                 200                 205

Val Asp Ile Tyr Glu Pro Ile Ala Thr Tyr Thr Ile Pro Gly Pro Pro
    210                 215                 220

Glu Pro Thr Phe
225

<210> SEQ ID NO 17
<211> LENGTH: 506
<212> TYPE: PRT
<213> ORGANISM: Aspergillus fumigatus

<400> SEQUENCE: 17

Gln Gln Val Gly Thr Ser Gln Ala Glu Val His Pro Ser Met Thr Trp
1               5                   10                  15

Gln Ser Cys Thr Ala Gly Gly Ser Cys Thr Thr Asn Asn Gly Lys Val
                20                  25                  30

Val Ile Asp Ala Asn Trp Arg Trp Val His Lys Val Gly Asp Tyr Thr
            35                  40                  45

Asn Cys Tyr Thr Gly Asn Thr Trp Asp Thr Thr Ile Cys Pro Asp Asp
 50                  55                  60

Ala Thr Cys Ala Ser Asn Cys Ala Leu Glu Gly Ala Asn Tyr Glu Ser
 65                  70                  75                  80

Thr Tyr Gly Val Thr Ala Ser Gly Asn Ser Leu Arg Leu Asn Phe Val
                85                  90                  95

Thr Thr Ser Gln Gln Lys Asn Ile Gly Ser Arg Leu Tyr Met Met Lys
                100                 105                 110

Asp Asp Ser Thr Tyr Glu Met Phe Lys Leu Leu Asn Gln Glu Phe Thr
                115                 120                 125
```

Phe Asp Val Asp Val Ser Asn Leu Pro Cys Gly Leu Asn Gly Ala Leu
    130                 135                 140

Tyr Phe Val Ala Met Asp Ala Asp Gly Gly Met Ser Lys Tyr Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Gln Pro Ser Ser Asn Asp Ala Asn Ala Gly Thr Gly Asn His Gly Ser
        195                 200                 205

Cys Cys Ala Glu Met Asp Ile Trp Glu Ala Asn Ser Ile Ser Thr Ala
210                 215                 220

Phe Thr Pro His Pro Cys Asp Thr Pro Gly Gln Val Met Cys Thr Gly
225                 230                 235                 240

Asp Ala Cys Gly Gly Thr Tyr Ser Ser Asp Arg Tyr Gly Gly Thr Cys
                245                 250                 255

Asp Pro Asp Gly Cys Asp Phe Asn Ser Phe Arg Gln Gly Asn Lys Thr
            260                 265                 270

Phe Tyr Gly Pro Gly Met Thr Val Asp Thr Lys Ser Lys Phe Thr Val
275                 280                 285

Val Thr Gln Phe Ile Thr Asp Asp Gly Thr Ser Ser Gly Thr Leu Lys
290                 295                 300

Glu Ile Lys Arg Phe Tyr Val Gln Asn Gly Lys Val Ile Pro Asn Ser
305                 310                 315                 320

Glu Ser Thr Trp Thr Gly Val Ser Gly Asn Ser Ile Thr Thr Glu Tyr
                325                 330                 335

Cys Thr Ala Gln Lys Ser Leu Phe Gln Asp Gln Asn Val Phe Glu Lys
            340                 345                 350

His Gly Gly Leu Glu Gly Met Gly Ala Ala Leu Ala Gln Gly Met Val
        355                 360                 365

Leu Val Met Ser Leu Trp Asp Asp His Ser Ala Asn Met Leu Trp Leu
370                 375                 380

Asp Ser Asn Tyr Pro Thr Thr Ala Ser Ser Thr Thr Pro Gly Val Ala
385                 390                 395                 400

Arg Gly Thr Cys Asp Ile Ser Ser Gly Val Pro Ala Asp Val Glu Ala
                405                 410                 415

Asn His Pro Asp Ala Tyr Val Val Tyr Ser Asn Ile Lys Val Gly Pro
            420                 425                 430

Ile Gly Ser Thr Phe Asn Ser Gly Gly Ser Asn Pro Gly Gly Gly Thr
        435                 440                 445

Thr Thr Thr Thr Thr Thr Gln Pro Thr Thr Thr Thr Thr Thr Ala Gly
450                 455                 460

Asn Pro Gly Gly Thr Gly Val Ala Gln His Tyr Gly Gln Cys Gly Gly
465                 470                 475                 480

Ile Gly Trp Thr Gly Pro Thr Thr Cys Ala Ser Pro Tyr Thr Cys Gln
                485                 490                 495

Lys Leu Asn Asp Tyr Tyr Ser Gln Cys Leu
            500                 505

<210> SEQ ID NO 18
<211> LENGTH: 435
<212> TYPE: PRT
<213> ORGANISM: Aspergillus fumigatus

```
<400> SEQUENCE: 18

Gln Gln Thr Val Trp Gly Gln Cys Gly Gly Gln Gly Trp Ser Gly Pro
1               5                   10                  15

Thr Ser Cys Val Ala Gly Ala Ala Cys Ser Thr Leu Asn Pro Tyr Tyr
            20                  25                  30

Ala Gln Cys Ile Pro Gly Ala Thr Ala Ser Thr Thr Leu Thr Thr
        35                  40                  45

Thr Thr Ala Ala Thr Thr Thr Ser Gln Thr Thr Lys Pro Thr Thr
50                  55                  60

Thr Gly Pro Thr Thr Ser Ala Pro Thr Val Thr Ala Ser Gly Asn Pro
65                  70                  75                  80

Phe Ser Gly Tyr Gln Leu Tyr Ala Asn Pro Tyr Tyr Ser Ser Glu Val
                85                  90                  95

His Thr Leu Ala Met Pro Ser Leu Pro Ser Ser Leu Gln Pro Lys Ala
            100                 105                 110

Ser Ala Val Ala Glu Val Pro Ser Phe Val Trp Leu Asp Val Ala Ala
            115                 120                 125

Lys Val Pro Thr Met Gly Thr Tyr Leu Ala Asp Ile Gln Ala Lys Asn
130                 135                 140

Lys Ala Gly Ala Asn Pro Pro Ile Ala Gly Ile Phe Val Val Tyr Asp
145                 150                 155                 160

Leu Pro Asp Arg Asp Cys Ala Ala Leu Ala Ser Asn Gly Glu Tyr Ser
                165                 170                 175

Ile Ala Asn Asn Gly Val Ala Asn Tyr Lys Ala Tyr Ile Asp Ala Ile
            180                 185                 190

Arg Ala Gln Leu Val Lys Tyr Ser Asp Val His Thr Ile Leu Val Ile
        195                 200                 205

Glu Pro Asp Ser Leu Ala Asn Leu Val Thr Asn Leu Asn Val Ala Lys
210                 215                 220

Cys Ala Asn Ala Gln Ser Ala Tyr Leu Glu Cys Val Asp Tyr Ala Leu
225                 230                 235                 240

Lys Gln Leu Asn Leu Pro Asn Val Ala Met Tyr Leu Asp Ala Gly His
                245                 250                 255

Ala Gly Trp Leu Gly Trp Pro Ala Asn Leu Gly Pro Ala Ala Thr Leu
            260                 265                 270

Phe Ala Lys Val Tyr Thr Asp Ala Gly Ser Pro Ala Ala Val Arg Gly
            275                 280                 285

Leu Ala Thr Asn Val Ala Asn Tyr Asn Ala Trp Ser Leu Ser Thr Cys
290                 295                 300

Pro Ser Tyr Thr Gln Gly Asp Pro Asn Cys Asp Glu Lys Lys Tyr Ile
305                 310                 315                 320

Asn Ala Met Ala Pro Leu Leu Lys Glu Ala Gly Phe Asp Ala His Phe
                325                 330                 335

Ile Met Asp Thr Ser Arg Asn Gly Val Gln Pro Thr Lys Gln Asn Ala
            340                 345                 350

Trp Gly Asp Trp Cys Asn Val Ile Gly Thr Gly Phe Gly Val Arg Pro
        355                 360                 365

Ser Thr Asn Thr Gly Asp Pro Leu Gln Asp Ala Phe Val Trp Ile Lys
370                 375                 380

Pro Gly Gly Glu Ser Asp Gly Thr Ser Asn Ser Thr Ser Pro Arg Tyr
385                 390                 395                 400

Asp Ala His Cys Gly Tyr Ser Asp Ala Leu Gln Pro Ala Pro Glu Ala
                405                 410                 415
```

Gly Thr Trp Phe Gln Ala Tyr Phe Glu Gln Leu Leu Thr Asn Ala Asn
              420                 425                 430

Pro Ser Phe
        435

<210> SEQ ID NO 19
<211> LENGTH: 547
<212> TYPE: PRT
<213> ORGANISM: Meripilus giganteus

<400> SEQUENCE: 19

Thr Pro Thr Gly Arg Asn Leu Lys Leu His Glu Ala Arg Glu Asp Leu
1               5                   10                  15

Pro Ala Gly Phe Ser Leu Arg Gly Ala Ala Ser Pro Asp Thr Thr Leu
            20                  25                  30

Lys Leu Arg Ile Ala Leu Val Gln Asn Asn Phe Ala Glu Leu Glu Asp
        35                  40                  45

Lys Leu Tyr Asp Val Ser Thr Pro Ser Ala Asn Tyr Gly Asn His
    50                  55                  60

Leu Ser Lys Glu Glu Val Glu Gln Tyr Ile Ala Pro Ala Pro Glu Ser
65                  70                  75                  80

Val Lys Ala Val Asn Ala Trp Leu Thr Glu Asn Gly Leu Asp Ala His
                85                  90                  95

Thr Ile Ser Pro Ala Gly Asp Trp Leu Ala Phe Glu Val Pro Val Ser
            100                 105                 110

Lys Ala Asn Glu Leu Phe Asp Ala Asp Phe Ser Val Phe Thr His Asp
        115                 120                 125

Glu Ser Gly Leu Glu Ala Ile Arg Thr Leu Ala Tyr Ser Ile Pro Ala
130                 135                 140

Glu Leu Gln Gly His Leu Asp Leu Val His Pro Thr Val Thr Phe Pro
145                 150                 155                 160

Asn Pro Asn Ala His Leu Pro Val Val Arg Ser Thr Gln Pro Ile Arg
                165                 170                 175

Asn Leu Thr Gly Arg Ala Ile Pro Ala Ser Cys Ala Ser Thr Ile Thr
            180                 185                 190

Pro Ala Cys Leu Gln Ala Ile Tyr Gly Ile Pro Thr Thr Lys Ala Thr
        195                 200                 205

Gln Ser Ser Asn Lys Leu Ala Val Ser Gly Phe Ile Asp Gln Phe Ala
    210                 215                 220

Asn Lys Ala Asp Leu Lys Ser Phe Leu Ala Gln Phe Arg Lys Asp Ile
225                 230                 235                 240

Ser Ser Ser Thr Thr Phe Ser Leu Gln Thr Leu Asp Gly Gly Glu Asn
                245                 250                 255

Asp Gln Ser Pro Ser Glu Ala Gly Ile Glu Ala Asn Leu Asp Ile Gln
            260                 265                 270

Tyr Thr Val Gly Leu Ala Thr Gly Val Pro Thr Thr Phe Ile Ser Val
        275                 280                 285

Gly Asp Asp Phe Gln Asp Gly Asn Leu Glu Gly Phe Leu Asp Ile Ile
    290                 295                 300

Asn Phe Leu Leu Gly Glu Ser Asn Pro Pro Gln Val Leu Thr Thr Ser
305                 310                 315                 320

Tyr Gly Gln Asn Glu Asn Thr Ile Ser Ala Lys Leu Ala Asn Gln Leu
                325                 330                 335

Cys Asn Ala Tyr Ala Gln Leu Gly Ala Arg Gly Thr Ser Ile Leu Phe
            340                 345                 350

```
Ala Ser Gly Asp Gly Gly Val Ser Gly Ser Gln Ser Ala His Cys Ser
        355             360             365

Asn Phe Val Pro Thr Phe Pro Ser Gly Cys Pro Phe Met Thr Ser Val
    370             375             380

Gly Ala Thr Gln Gly Val Ser Pro Glu Thr Ala Ala Ala Phe Ser Ser
385             390             395                         400

Gly Gly Phe Ser Asn Val Phe Gly Ile Pro Ser Tyr Gln Ala Ser Ala
            405             410                     415

Val Ser Gly Tyr Leu Ser Ala Leu Gly Ser Thr Asn Ser Gly Lys Phe
            420             425             430

Asn Arg Ser Gly Arg Gly Phe Pro Asp Val Ser Thr Gln Gly Val Asp
        435             440             445

Phe Gln Ile Val Ser Gly Gly Gln Thr Ile Gly Val Asp Gly Thr Ser
    450             455             460

Cys Ala Ser Pro Thr Phe Ala Ser Val Ile Ser Leu Val Asn Asp Arg
465             470             475                         480

Leu Ile Ala Ala Gly Lys Ser Pro Leu Gly Phe Leu Asn Pro Phe Leu
            485             490             495

Tyr Ser Ser Ala Gly Lys Ala Ala Leu Asn Asp Val Thr Ser Gly Ser
            500             505             510

Asn Pro Gly Cys Ser Thr Asn Gly Phe Pro Ala Lys Ala Gly Trp Asp
        515             520             525

Pro Val Thr Gly Leu Gly Thr Pro Asn Phe Ala Lys Leu Leu Thr Ala
        530             535             540

Val Gly Leu
545
```